United States Patent
Locke et al.

(10) Patent No.: US 12,365,933 B2
(45) Date of Patent: *Jul. 22, 2025

(54) SYSTEMS AND METHODS FOR EPIGENETIC ANALYSIS

(71) Applicant: Seven Bridges Genomics Inc., Charlestown, MA (US)

(72) Inventors: Devin Locke, Medford, MA (US); Wan-Ping Lee, Somerville, MA (US)

(73) Assignee: Seven Bridges Genomics Inc., Charlestown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/329,431

(22) Filed: Jun. 5, 2023

(65) Prior Publication Data

US 2024/0011074 A1    Jan. 11, 2024

Related U.S. Application Data

(63) Continuation of application No. 17/023,289, filed on Sep. 16, 2020, now Pat. No. 11,697,835, which is a continuation of application No. 15/007,874, filed on Jan. 27, 2016, now Pat. No. 10,793,895.

(60) Provisional application No. 62/209,058, filed on Aug. 24, 2015.

(51) Int. Cl.
*G01N 33/48* (2006.01)
*C12Q 1/6806* (2018.01)
*C12Q 1/6869* (2018.01)
*C12Q 1/6874* (2018.01)
*G16B 30/00* (2019.01)
*G16B 30/10* (2019.01)

(52) U.S. Cl.
CPC ......... *C12Q 1/6806* (2013.01); *C12Q 1/6869* (2013.01); *C12Q 1/6874* (2013.01); *G16B 30/00* (2019.02); *G16B 30/10* (2019.02)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,988,617 A | 1/1991 | Landegren et al. | |
| 5,234,809 A | 8/1993 | Boom et al. | |
| 5,242,794 A | 9/1993 | Whiteley et al. | |
| 5,494,810 A | 2/1996 | Barany et al. | |
| 5,511,158 A | 4/1996 | Sims | |
| 5,583,024 A | 12/1996 | McElroy et al. | |
| 5,674,713 A | 10/1997 | McElroy et al. | |
| 5,700,673 A | 12/1997 | McElroy et al. | |
| 5,701,256 A | 12/1997 | Marr et al. | |
| 6,054,278 A | 4/2000 | Dodge et al. | |
| 6,210,891 B1 | 4/2001 | Nyren et al. | |
| 6,223,128 B1 | 4/2001 | Allex et al. | |
| 6,306,597 B1 | 10/2001 | Macevicz | |
| 6,582,938 B1 | 6/2003 | Su et al. | |
| 6,818,395 B1 | 11/2004 | Quake et al. | |
| 6,828,100 B1 | 12/2004 | Ronaghi | |
| 6,833,246 B2 | 12/2004 | Balasubramanian | |
| 6,890,763 B2 | 5/2005 | Jackowski et al. | |
| 6,911,345 B2 | 6/2005 | Quake et al. | |
| 6,925,389 B2 | 8/2005 | Hitt et al. | |
| 6,989,100 B2 | 1/2006 | Norton | |
| 7,169,560 B2 | 1/2007 | Lapidus et al. | |
| 7,232,656 B2 | 6/2007 | Balasubramanian et al. | |
| 7,282,337 B1 | 10/2007 | Harris | |
| 7,321,623 B2 | 1/2008 | Dambrackas | |
| 7,483,585 B2 | 1/2009 | Brakus, Jr. | |
| 7,577,554 B2 | 8/2009 | Lystad et al. | |
| 7,580,918 B2 | 8/2009 | Chang et al. | |
| 7,598,035 B2 | 10/2009 | Macevicz | |
| 7,620,800 B2 | 11/2009 | Huppenthal et al. | |
| 7,776,616 B2 | 8/2010 | Heath et al. | |
| 7,809,509 B2 | 10/2010 | Milosavljevic | |
| 7,835,871 B2 | 11/2010 | Kain et al. | |
| 7,885,840 B2 | 2/2011 | Sadiq et al. | |
| 7,917,302 B2 | 3/2011 | Rognes | |
| 7,957,913 B2 | 6/2011 | Chinitz et al. | |
| 7,960,120 B2 | 6/2011 | Rigatti et al. | |

(Continued)

FOREIGN PATENT DOCUMENTS

KR         101282798 B1    7/2013
WO    WO 2007/086935 A2   8/2007

(Continued)

OTHER PUBLICATIONS

Li, Yuanyuan, and Trygve O. Tollefsbol. "DNA methylation detection: bisulfite genomic sequencing analysis." Epigenetics protocols (2011): 11-21.*

(Continued)

*Primary Examiner* — Anna Skibinsky
(74) *Attorney, Agent, or Firm* — Wolf, Greenfield & Sacks, P.C.

(57) ABSTRACT

The invention provides systems and methods for determining patterns of modification to a genome of a subject by representing the genome using a graph, such as a directed acyclic graph (DAG) with divergent paths for regions that are potentially subject to modification, profiling segments of the genome for evidence of epigenetic modification, and aligning the profiled segments to the DAG to determine locations and patterns of the epigenetic modification within the genome.

20 Claims, 9 Drawing Sheets

(56) References Cited

U.S. PATENT DOCUMENTS

| | | |
|---|---|---|
| 8,146,099 B2 | 3/2012 | Tkatch et al. |
| 8,165,821 B2 | 4/2012 | Zhang |
| 8,209,130 B1 | 6/2012 | Kennedy et al. |
| 8,340,914 B2 | 12/2012 | Gatewood et al. |
| 8,370,079 B2 | 2/2013 | Sorenson et al. |
| 8,639,847 B2 | 1/2014 | Blaszczak et al. |
| 8,972,201 B2 | 3/2015 | Mande et al. |
| 9,063,914 B2 | 6/2015 | Kural et al. |
| 9,092,402 B2 | 7/2015 | Kural et al. |
| 9,116,866 B2 | 8/2015 | Kural |
| 9,390,226 B2 | 7/2016 | Kural |
| 9,817,944 B2 | 11/2017 | Kural |
| 10,584,380 B2 | 3/2020 | Locke et al. |
| 10,724,110 B2 | 7/2020 | Locke et al. |
| 10,793,895 B2 | 10/2020 | Locke et al. |
| 11,649,495 B2 | 5/2023 | Locke et al. |
| 11,697,835 B2 | 7/2023 | Locke et al. |
| 11,702,708 B2 | 7/2023 | Locke et al. |
| 2002/0164629 A1 | 11/2002 | Quake et al. |
| 2002/0190663 A1 | 12/2002 | Rasmussen |
| 2003/0032026 A1 | 2/2003 | Berlin |
| 2004/0023209 A1 | 2/2004 | Jonasson |
| 2005/0089906 A1 | 4/2005 | Furuta et al. |
| 2006/0024681 A1 | 2/2006 | Smith et al. |
| 2006/0195269 A1 | 8/2006 | Yeatman et al. |
| 2006/0292611 A1 | 12/2006 | Berka et al. |
| 2007/0087365 A1 | 4/2007 | Van Criekinge et al. |
| 2007/0114362 A1 | 5/2007 | Feng et al. |
| 2007/0166707 A1 | 7/2007 | Schadt et al. |
| 2007/0218467 A1 | 9/2007 | Ecker et al. |
| 2008/0003571 A1 | 1/2008 | McKernan et al. |
| 2008/0077607 A1 | 3/2008 | Gatawood et al. |
| 2008/0251711 A1 | 10/2008 | Reilly |
| 2008/0281463 A1 | 11/2008 | Suh et al. |
| 2008/0294403 A1 | 11/2008 | Zhu et al. |
| 2009/0026082 A1 | 1/2009 | Rothberg et al. |
| 2009/0119313 A1 | 5/2009 | Pearce |
| 2009/0127589 A1 | 5/2009 | Rothberg et al. |
| 2009/0164135 A1 | 6/2009 | Brodzik et al. |
| 2009/0191565 A1 | 7/2009 | Lapidus et al. |
| 2009/0233809 A1 | 9/2009 | Faham et al. |
| 2009/0300781 A1 | 12/2009 | Bancroft et al. |
| 2009/0318310 A1 | 12/2009 | Liu et al. |
| 2009/0325145 A1 | 12/2009 | Sablon et al. |
| 2010/0010992 A1 | 1/2010 | Morris |
| 2010/0035252 A1 | 2/2010 | Rothberg et al. |
| 2010/0041048 A1 | 2/2010 | Diehi et al. |
| 2010/0137143 A1 | 6/2010 | Rothberg et al. |
| 2010/0169026 A1 | 7/2010 | Sorenson et al. |
| 2010/0188073 A1 | 7/2010 | Rothberg et al. |
| 2010/0197507 A1 | 8/2010 | Rothberg et al. |
| 2010/0240046 A1 | 9/2010 | Palmer et al. |
| 2010/0282617 A1 | 11/2010 | Rothberg et al. |
| 2010/0285578 A1 | 11/2010 | Selden et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2011/0004413 A1 | 1/2011 | Carnevali et al. |
| 2011/0009278 A1 | 1/2011 | Kain et al. |
| 2011/0098193 A1 | 4/2011 | Kingsmore et al. |
| 2011/0207135 A1 | 8/2011 | Faham et al. |
| 2011/0257889 A1 | 10/2011 | Klammer et al. |
| 2012/0030566 A1 | 2/2012 | Victor |
| 2012/0040851 A1 | 2/2012 | Lieberman et al. |
| 2012/0041727 A1 | 2/2012 | Mishra et al. |
| 2012/0045771 A1 | 2/2012 | Beier et al. |
| 2012/0157322 A1 | 6/2012 | Myllykangas et al. |
| 2012/0239706 A1 | 9/2012 | Steinfadt |
| 2012/0330566 A1 | 12/2012 | Chaisson |
| 2013/0029879 A1 | 1/2013 | Shelly et al. |
| 2013/0035904 A1 | 2/2013 | Kuhn |
| 2013/0059738 A1 | 3/2013 | Leamon et al. |
| 2013/0059740 A1 | 3/2013 | Drmanac et al. |
| 2013/0073214 A1 | 3/2013 | Hyland et al. |
| 2013/0124100 A1 | 5/2013 | Drmanac et al. |
| 2013/0138358 A1 | 5/2013 | Tang et al. |
| 2013/0232480 A1 | 9/2013 | Winterfeldt et al. |
| 2013/0289099 A1 | 10/2013 | Le Goff et al. |
| 2013/0311106 A1 | 11/2013 | White et al. |
| 2013/0332081 A1 | 12/2013 | Reese et al. |
| 2013/0345066 A1 | 12/2013 | Brinza et al. |
| 2014/0012866 A1 | 1/2014 | Bowman et al. |
| 2014/0025312 A1 | 1/2014 | Chin et al. |
| 2014/0051588 A9 | 2/2014 | Drmanac et al. |
| 2014/0066317 A1 | 3/2014 | Talasaz |
| 2014/0129201 A1 | 5/2014 | Kennedy et al. |
| 2014/0136120 A1 | 5/2014 | Colwell et al. |
| 2014/0195564 A1 | 7/2014 | Talagala et al. |
| 2014/0200147 A1 | 7/2014 | Bartha et al. |
| 2014/0278590 A1 | 9/2014 | Abbassi et al. |
| 2014/0280360 A1 | 9/2014 | Webber et al. |
| 2014/0281708 A1 | 9/2014 | Adam et al. |
| 2014/0323320 A1 | 10/2014 | Jia et al. |
| 2014/0371110 A1 | 12/2014 | Van Rooyen et al. |
| 2015/0020061 A1 | 1/2015 | Ravi |
| 2015/0056613 A1 | 2/2015 | Kural |
| 2015/0057946 A1 | 2/2015 | Kural |
| 2015/0066383 A1 | 3/2015 | Wernicke |
| 2015/0094212 A1 | 4/2015 | Gottimukkala et al. |
| 2015/0110754 A1 | 4/2015 | Bai et al. |
| 2015/0112602 A1 | 4/2015 | Kural et al. |
| 2015/0112658 A1 | 4/2015 | Kural et al. |
| 2015/0197815 A1 | 7/2015 | Kural |
| 2015/0199472 A1 | 7/2015 | Kural |
| 2015/0199473 A1 | 7/2015 | Kural |
| 2015/0199474 A1 | 7/2015 | Kural |
| 2015/0199475 A1 | 7/2015 | Kural |
| 2015/0227685 A1 | 8/2015 | Kural |
| 2015/0293994 A1 | 10/2015 | Kelly |
| 2015/0302145 A1 | 10/2015 | Kural et al. |
| 2015/0310167 A1 | 10/2015 | Kural et al. |
| 2015/0344970 A1 | 12/2015 | Vogelstein et al. |
| 2015/0347678 A1 | 12/2015 | Kural |
| 2015/0356147 A1 | 12/2015 | Mishra et al. |
| 2016/0259880 A1 | 9/2016 | Semenyuk |
| 2016/0306921 A1 | 10/2016 | Kural |
| 2016/0342737 A1 | 11/2016 | Kaye |
| 2016/0355881 A1 | 12/2016 | Wangh et al. |
| 2016/0364523 A1 | 12/2016 | Locke et al. |
| 2017/0058320 A1 | 3/2017 | Locke et al. |
| 2017/0058341 A1 | 3/2017 | Locke et al. |
| 2017/0058365 A1 | 3/2017 | Locke et al. |
| 2017/0198351 A1 | 7/2017 | Lee et al. |
| 2017/0199959 A1 | 7/2017 | Locke |
| 2017/0199960 A1 | 7/2017 | Ghose et al. |
| 2017/0242958 A1 | 8/2017 | Brown |
| 2020/0232029 A1 | 7/2020 | Locke et al. |
| 2020/0399719 A1 | 12/2020 | Locke et al. |
| 2020/0407778 A1 | 12/2020 | Locke et al. |
| 2023/0357842 A1 | 11/2023 | Locke et al. |
| 2023/0366046 A1 | 11/2023 | Locke et al. |

FOREIGN PATENT DOCUMENTS

| | | |
|---|---|---|
| WO | WO 2010/010992 A1 | 1/2010 |
| WO | WO 2012/096579 A2 | 7/2012 |
| WO | WO 2012/098515 A1 | 7/2012 |
| WO | WO 2012/142531 A2 | 10/2012 |
| WO | WO 2013/035904 A1 | 3/2013 |
| WO | WO 2013/043909 A1 | 3/2013 |
| WO | WO 2013/106737 A1 | 7/2013 |
| WO | WO 2013/184643 A1 | 12/2013 |
| WO | WO 2015/027050 A1 | 2/2015 |
| WO | WO 2015/048753 A1 | 4/2015 |
| WO | WO 2015/058093 A1 | 4/2015 |
| WO | WO 2015/058095 A1 | 4/2015 |
| WO | WO 2015/058097 A1 | 4/2015 |
| WO | WO 2015/058120 A1 | 4/2015 |
| WO | WO 2015/061099 A1 | 4/2015 |
| WO | WO 2015/061103 A1 | 4/2015 |
| WO | WO 2015/105963 A1 | 7/2015 |
| WO | WO 2015/123269 A1 | 8/2015 |
| WO | WO 2016/141294 A1 | 9/2016 |

(56) References Cited

FOREIGN PATENT DOCUMENTS

| WO | WO 2016/201215 A1 | 12/2016 |
|---|---|---|
| WO | WO 2017/120128 A1 | 7/2017 |
| WO | WO 2017/123864 A1 | 7/2017 |
| WO | WO 2017/147124 A1 | 8/2017 |

OTHER PUBLICATIONS

Communication pursuant to Article 94(3) EPC issued Apr. 21, 2017 in European Application No. 14803268.3.
Examination Report issued Mar. 1, 2018 for Singapore Application No. 11201601124Y.
Extended European Search Report issued Mar. 29, 2017 in European Application No. 14837955.5.
Extended European Search Report issued May 9, 2017 in European Application No. 14847490.1.
Extended European Search Report issued Apr. 12, 2017 in European Application No. 14854801.9.
International Preliminary Report on Patentability for International Application No. PCT/US2014/052065 mailed Feb. 23, 2016.
International Search Report and Written Opinion for International Application No. PCT/US2014/061158 mailed Feb. 4, 2015.
International Search Report and Written Opinion for International Application No. PCT/US2014/058328 mailed Dec. 30, 2014.
International Search Report and Written Opinion for International Application No. PCT/US2014/061198 mailed Feb. 4, 2015.
International Search Report and Written Opinion for International Application No. PCT/US2014/061162 mailed Mar. 19, 2015.
International Search Report and Written Opinion for International Application No. PCT/US2016/057324 mailed Jan. 10, 2017.
International Search Report and Written Opinion for International Application No. PCT/US2016/036873 mailed Sep. 7, 2016.
International Search Report and Written Opinion for International Application No. PCT/US2014/061156 mailed Feb. 17, 2015.
International Search Report and Written Opinion for International Application No. PCT/US2014/052065 mailed Dec. 11, 2014.
International Search Report and Written Opinion for International Application No. PCT/US2014/060680 mailed Jan. 27, 2015.
International Search Report and Written Opinion for International Application No. PCT/US2014/060690 mailed Feb. 10, 2015.
International Search Report and Written Opinion for International Application No. PCT/US2015/010604 mailed Mar. 31, 2015.
International Search Report and Written Opinion for International Application No. PCT/US2015/015375 mailed May 11, 2015.
International Search Report and Written Opinion for International Application No. PCT/US2016/020899 mailed May 5, 2016.
International Search Report and Written Opinion for International Application No. PCT/US2017/013329 mailed Apr. 7, 2017.
International Search Report and Written Opinion for International Application No. PCT/US2017/012015 mailed Apr. 19, 2017.
International Search Report and Written Opinion for International Application No. PCT/US2017/018830 mailed Aug. 31, 2017.
International Search Report and Written Opinion for International Application No. PCT/US2015/054461 mailed Jan. 5, 2016.
International Search Report and Written Opinion for International Application No. PCT/US2016/033201 mailed Sep. 2, 2016 (14 pages).
International Search Report and Written Opinion for International Application No. PCT/US2015/048891 mailed Nov. 17, 2015.
Written Opinion issued Dec. 21, 2016 for Singapore Application No. 11201601124Y.
Written Opinion issued May 29, 2017 for Singapore Application No. 11201602903X.
Written Opinion issued Jun. 12, 2017 for Singapore Application No. 11201603039P.
Written Opinion issued Jul. 10, 2017 for Singapore Application No. 11201603044S.
Written Opinion issued Jun. 15, 2017 for Singapore Application No. 11201605506Q.

[No Author Listed], BCF2 Quick Reference (r198). http://samtools.github.io/hts-specs/BCFv2_gref.pdf [last accessed Nov. 13, 2019]. 1 page.
[No Author Listed], Directed acyclic graph. 2013. 6 pages. https://atozwiki.com/Directed_acyclic_graph [Last accessed Jul. 27, 2022].
[No Author Listed], The Variant Call Formal (VCF) Version 4.2 Specification. Jul. 8, 2019. https://samtools.github.io/hts-specs/VCFv4.2.pdf [last accessed Nov. 15, 2019]. 28 pages.
Abouelhoda et al., Integrating Taverna and Galaxy workflows with cloud computing support. BMC bioinformatics. Dec. 2012;13(1):77.
Agarwal et al., Social interaction network extractor from text. InThe Companion Volume of the Proceedings of IJCNLP 2013: System Demonstrations Oct. 2013: pp. 33-36.
Aguiar et al., HapCompass: a fast cycle basis algorithm for accurate haplotype assembly of sequence data. Journal of Computational Biology. Jun. 1, 2012;19(6):577-90.
Aguiar et al., Haplotype assembly in polyploid genomes and identical by descent shared tracts. Bioinformatics. Jun. 19, 2013;29(13):1352-60.
Airoldi et al., Mixed membership stochastic blockmodels. Journal of machine learning research. 2008;9(Sep.):1981-2014.
Albers et al., accurate indel calls from short-read data. Genome research. Jun. 1, 2011;21(6):961-73.
Alioto et al., A comprehensive assessment of somatic mutation detection in cancer using whole-genome sequencing. Nature communications. Dec. 9, 2015;6:10001.
Altera, Implementation of the Smith-Waterman algorithm on reconfigurable supercomputing platform, White Paper ver 1.0. 2007 (18 pages).
Altschul et al., Optimal sequence alignment using affine gap costs. Bulletin of mathematical biology. Jan. 1, 1986;48(5-6):603-16.
Auton et al., the 1000 Genomes Project Consortium. A global reference for human genetic variation. Nature. Oct. 2015;526(7571):68-74.
Bansal et al., An MCMC algorithm for haplotype assembly from whole-genome sequence data. Genome research. Aug. 1, 2008;18(8):1336-46.
Bao et al., BRANCH: boosting RNA-Seq assemblies with partial or related genomic sequences. Bioinformatics. Mar. 14, 2013;29(10):1250-9.
Barbieri et al., Exome sequencing identifies recurrent SPOP, FOXA1 and MED12 mutations in prostate cancer. Nature genetics. Jun. 2012;44(6):685-689.
Beerenwinkel et al., Conjunctive bayesian networks. Bernoulli. 2007;13(4):893-909.
Berlin et al., Assembling large genomes with single-molecule sequencing and locality-sensitive hashing. Nature biotechnology. Jun. 2015;33(6):623.bioRxiv preprint (35 pages); retrieved from the internet on Jan. 29, 2015, at <http://biorxiv.org/content/biorxiv/early/2014/08/14/008003.full.pdf>.
Bertone et al., Global identification of human transcribed sequences with genome tiling arrays. Science. Dec. 24, 2004;306(5705):2242-6.
Bertrand et al., Genetic map refinement using a comparative genomic approach. Journal of Computational Biology. Oct. 1, 2009;16(10):1475-86.
Black, A simple answer for a splicing conundrum. Proceedings of the National Academy of Sciences. Apr. 5, 2005;102(14):4927-8.
Borozan et al., Evaluation of alignment algorithms for discovery and identification of pathogens using RNA-Seq. PloS one. Oct. 30, 2013;8(10):e76935. 17 pages.
Boyer et al., A fast string searching algorithm. Communications of the ACM. Oct. 1, 1977;20(10):762-72.
Browning et al., Haplotype phasing: existing methods and new developments. Nature Reviews Genetics. Oct. 2011;12(10):703.
Buhler et al., Search algorithms for biosequences using random projection. University of Washington; Aug. 2001. (203 pages); retrieved from the internet on Jun. 3, 2016, at <http://www.mathcs.emory.edu/~cheung/papers/Matching/Search-Alg-for-Biosequences-Thesis.pdf>.
Caboche et al., Comparison of mapping algorithms used in high-throughput sequencing: application to Ion Torrent data. BMC genomics. Dec. 2014;15(1):264.

(56) References Cited

OTHER PUBLICATIONS

Carig et al., Ordering of cosmid clones covering the herpes simplex virus type I (HSV-I) genome: a test case for fingerprinting by hybridisation. Nucleic acids research. May 1, 1990;18(9):2653-60.
Carrington et al., Polypeptide ligation occurs during post-translational modification of concanavalin A. Nature. Jan. 1985;313(5997):64.
Cartwright, DNA assembly with gaps (Dawg): simulating sequence evolution. Bioinformatics. Nov. 1, 2005;21(Suppl_3):iii31-8.
Chang, The application of alternative splicing graphs in quantitative analysis of alternative splicing form from EST database, Int J Comp Appl Tech. 2005; 22(1):14.
Chen, Transient hypermutability, chromothripsis and replication-based mechanisms in the generation of concurrent clustered mutations, Mutation Res. 2012; 750(1):562-59.
Chin et al., Nonhybrid, finished microbial genome assemblies from long-read SMRT sequencing data. Nature methods. Jun. 2013;10(6):563-569.
Chuang et al., Gene recognition based on DAG shortest paths. Bioinformatics. Jun. 1, 2001;17(suppl_1):S56-64.
Clark, 2014, Illumina announces landmark $1,000 human genome sequencing, Wired, Jan. 15, 2014.
Cock et al., Galaxy tools and workflows for sequence analysis with applications in molecular plant pathology. PeerJ. Sep. 17, 2013;1:e167.
Cohen-Boulakia et al., Distilling structure in Taverna scientific workflows: a refactoring approach. BMC bioinformatics. Jan. 2014;15(1):S12.
Compeau et al., How to apply de Bruijn graphs to genome assembly. Nature biotechnology. Nov. 2011;29(11):987-991.
Cormen et al., Introduction to Algorithms. Third Edition. The MIT Press. 2009. 6 pages.
Costa, Uncovering the Complexity of Transcriptomes with RNA-Seq, J Biomed Biotech. 2010; 853916.
Craddock et al., Wellcome Trust Case Control Consortium. Genome-wide association study of 14,000 cases of seven common diseases and 3,000 shared controls. Nature. May 11, 2007;447:661-78.
Crochemore et al., Direct Construction of Compact Directed Acyclic Word Graphs. Springer, Berlin, Heidelberg. 1997:116-29.
Croft et al., The Use of Phrases and Structured Queries in Information Retrieval. Proceedings of the 14th Annual International ACM SIGIR Conference on Research and Development in Information Retrieval. 1991:32-45.
Danecek et al., The variant call format and VCFtools. Bioinformatics. Jun. 7, 2011;27(15):2156-8.
Delcher et al., Alignment of whole genomes. Nucleic acids research. Jan. 1, 1999;27(11):2369-76.
Denoeud et al., Identification of polymorphic tandem repeats by direct comparison of genome sequence from different bacterial strains: a web-based resource. BMC bioinformatics. Dec. 2004;5(1):4.
DePristo et al., A framework for variation discovery and genotyping using next-generation DNA sequencing data. Nature genetics. May 2011;43(5):491-498.
Dinov et al., Applications of the pipeline environment for visual informatics and genomics computations. BMC bioinformatics. Dec. 2011;12(1):304.
Do et al., Compressed Directed Acyclic Word Graph with Application in Local Alignment. Algorithmica. 2013;67:125-41.
Duan et al., Optimizing de novo common wheat transcriptome assembly using short-read RNA-Seq data. BMC genomics. Dec. 2012;13(1):392.
Dudley et al., A quick guide for developing effective bioinformatics programming skills. PLOS computational biology. Dec. 24, 2009;5(12):e1000589.
Durbin, Efficient haplotype matching and storage using the positional Burrows-Wheeler transform (PBWT). Bioinformatics. Jan. 9, 2014;30(9):1266-72.
Durham et al., EGene: a configurable pipeline generation system for automated sequence analysis. Bioinformatics. Apr. 6, 2005;21(12):2812-3.

Endelman JB. New algorithm improves fine structure of the barley consensus SNP map. BMC genomics. Dec. 2011;12(1):407.
Farrar, Striped Smith-Waterman speeds database searches six times over other SIMD implementations. Bioinformatics. Nov. 16, 2006;23(2):156-61.
Fiers et al., High-throughput bioinformatics with the Cyrille2 pipeline system. BMC bioinformatics. Dec. 2008;9(1):96.
Fitch, Distinguishing homologous from analogous proteins. Systematic zoology. Jun. 1, 1970;19(2):99-113.
Flicek et al., Sense from sequence reads: methods for alignment and assembly. Nature methods. Oct. 15, 2009;6(11s):S6-S12.
Florea et al., Gene and alternative splicing annotation with AIR. Genome research. Jan. 1, 2005;15(1):54-66.
Florea et al., Genome-guided transcriptome assembly in the age of next-generation sequencing. IEEE/ACM Transactions on Computational Biology and Bioinformatics (TCBB). Sep. 1, 2013;10(5):1234-40.
Floyd, Algorithm 245: treesort. Communications of the ACM. Dec. 1, 1964;7(12):701.
Garber et al., Computational methods for transcriptome annotation and quantification using RNA-seq. Nature methods. Jun. 2011;8(6):469-477.
Gerlinger et al., Intratumor heterogeneity and branched evolution revealed by multiregion sequencing. New England journal of medicine. Mar. 8, 2012;366(10):883-92.
Glusman et al., Whole-genome haplotyping approaches and genomic medicine. Genome medicine. Dec. 2014;6(9):73.
Golub et al., Molecular classification of cancer: class discovery and class prediction by gene expression monitoring. science. Oct. 15, 1999;286(5439):531-7.
Goto et al., BioRuby: bioinformatics software for the Ruby programming language. Bioinformatics. Aug. 25, 2010;26(20):2617-9.
Gotoh, An improved algorithm for matching biological sequences. Journal of molecular biology. Dec. 15, 1982;162(3):705-8.
Gotoh, Multiple sequence alignment: algorithms and applications. Advances in biophysics. Jan. 1, 1999;36:159-206.
Grabherr et al., Full-length transcriptome assembly from RNA-Seq data without a reference genome. Nature biotechnology. Jul. 2011;29(7):644-654.
Grasso et al., Combining partial order alignment and progressive multiple sequence alignment increases alignment speed and scalability to very large alignment problems. Bioinformatics. Feb. 12, 2004;20(10):1546-56.
Guttman et al., Ab initio reconstruction of cell type-specific transcriptomes in mouse reveals the conserved multi-exonic structure of lincRNAs. Nature biotechnology. May 2010;28(5):503-510.
Guttman, Ab initio reconstruction of transcriptomes of pluripotent and lineage committed cells reveals gene structures of thousands of lincRNAs, NIH-PA Author Manuscript. 2010.
Haas et al., DAGchainer: a tool for mining segmental genome duplications and synteny. Bioinformatics. Jul. 9, 2004;20(18):3643-6.
HapMap International Consortium. A haplotype map of the human genome. Nature. 2005;437:1299-320.
Harenberg et al., Community detection in large-scale networks: a survey and empirical evaluation. Wiley Interdisciplinary Reviews: Computational Statistics. Nov. 2014;6(6):426-39.
Harrow et al., GENCODE: the reference human genome annotation for The ENCODE Project. Genome research. Sep. 1, 2012;22(9):1760-74.
He et al., Optimal algorithms for haplotype assembly from whole-genome sequence data. Bioinformatics. Jun. 1, 2010;26(12):i183-90.
Heber et al., Splicing graphs and EST assembly problem. Bioinformatics. Jul. 1, 2002;18(suppl_1):S181-8.
Hein, A new method that simultaneously aligns and reconstructs ancestral sequences for any number of homologous sequences, when the phylogeny is given. Molecular Biology and Evolution. Nov. 1, 1989;6(6):649-68.
Hein, A tree reconstruction method that is economical in the number of pairwise comparisons used. Molecular biology and evolution. Nov. 1, 1989;6(6):669-84.

(56) References Cited

OTHER PUBLICATIONS

Hendren et al., Parallelizing Programs with Recursive Data Structures. IEEE Transactions on Parallel and Distributed Systems. 1990;1(1):35-47.
Hokamp et al., Wrapping up BLAST and other applications for use on Unix clusters. Bioinformatics. Feb. 12, 2003;19(3):441-2.
Holland et al., BioJava: an open-source framework for bioinformatics. Bioinformatics. Aug. 8, 2008;24(18):2096-7.
Homer et al., Improved variant discovery through local re-alignment of short-read next-generation sequencing data using SRMA. Genome biology. Oct. 2010;11(10):R99.
Hoon et al., Biopipe: a flexible framework for protocol-based bioinformatics analysis. Genome Research. Aug. 1, 2003;13(8):1904-15.
Horspool, Practical fast searching in strings. Software: Practice and Experience. Jun. 1980;10(6):501-6.
Huang, 3: Bio-Sequence Comparison and Alignment, ser. Curr Top Comp Mol Biol. Cambridge, Mass.: The MIT Press. 2002:45-69.
Huddleston et al., A new data structure for representing sorted lists. Acta informatica. Jun. 1, 1982;17(2):157-84.
Hull et al., Taverna: a tool for building and running workflows of services. Nucleic acids research. Jul. 1, 2006;34(suppl_2):W729-32.
Hutchinson et al., Allele-specific methylation occurs at genetic variants associated with complex disease. PloS one. Jun. 9, 2014;9(6):e98464.
Jones et al., AliWABA: alignment on the web through an A-Bruijn approach. Nucleic Acids Research. 2006;34:613-6.
Kano et al., Text mining meets workflow: linking U-Compare with Taverna. Bioinformatics. Aug. 12, 2010;26(19):2486-7.
Katoh et al., MAFFT version 5: improvement in accuracy of multiple sequence alignment. Nucleic acids research. Jan. 1, 2005;33(2):511-8.
Kawas et al., BioMoby extensions to the Taverna workflow management and enactment software. BMC bioinformatics. Dec. 2006;7(1):523.
Kehr et al., Genome alignment with graph data structures: a comparison. BMC bioinformatics. Dec. 2014;15(1):99.
Kent, BLAT—the BLAST-like alignment tool. Genome research. Apr. 1, 2002;12(4):656-64.
Kim et al., ECgene: genome-based EST clustering and gene modeling for alternative splicing. Genome research. Apr. 1, 2005;15(4):566-76.
Kim et al., Introducing EzTaxon-e: a prokaryotic 16S rRNA gene sequence database with phylotypes that represent uncultured species. International Journal of Systematic and Evolutionary Microbiology. 2012;62:716-21.
Kim et al., TopHat2: accurate alignment of transcriptomes in the presence of insertions, deletions and gene fusions. Genome biology. Apr. 2013;14(4):R36.
Kim et al.,. A scaffold analysis tool using mate-pair information in genome sequencing. BioMed Research International. Apr. 3, 2008; 8(3): 195-197.
Koolen et al., Clinical and molecular delineation of the 17q21. 31 microdeletion syndrome. Journal of medical genetics. Nov. 1, 2008;45(11):710-20.
Krabbenhöft et al., Integrating ARC grid middleware with Taverna workflows. Bioinformatics. Mar. 19, 2008;24(9):1221-2.
Kuhn et al., CDK-Taverna: an open workflow environment for cheminformatics. Bmc Bioinformatics. Dec. 2010;11(1):159.
Kumar et al., Comparing de novo assemblers for 454 transcriptome data. BMC genomics. Dec. 2010;11(1):571.
Kurtz et al., Versatile and open software for comparing large genomes. Genome biology. Jan. 2004;5(2):R12.
LaFramboise, Single nucleotide polymorphism arrays: a decade of biological, computational and technological advances. Nucleic acids research. Jul. 1, 2009;37(13):4181-93.
Lam et al., Compressed indexing and local alignment of DNA. Bioinformatics. Jan. 28, 2008;24(6):791-7.

Langmead et al., Ultrafast and memory-efficient alignment of short DNA sequences to the human genome. Genome biology. Mar. 2009;10(3):R25.
Lanzén et al., The Taverna Interaction Service: enabling manual interaction in workflows. Bioinformatics. Mar. 12, 2008;24(8):1118-20.
Larkin et al., Clustal W and Clustal X version 2.0. bioinformatics. Nov. 1, 2007;23(21):2947-8.
Layer et al., Efficient genotype compression and analysis of large genetic-variation datasets. Nature Methods. 2016;13(1):63-5.
Lecca et al., Defining order and timing of mutations during cancer progression: the TO-DAG probabilistic graphical model. Frontiers in genetics. Oct. 13, 2015;6:309: 1-17.
Lee et al. Accurate read mapping using a graph-based human pan-genome. (May 2015) American Society of Human Genetics 64th Annual Meeting Platform Abstracts; Abstract 41.
Lee et al., MOSAIK: a hash-based algorithm for accurate next-generation sequencing short-read mapping. PloS one. Mar. 5, 2014;9(3):e90581.
Lee et al., Multiple sequence alignment using partial order graphs. Bioinformatics. Mar. 1, 2002;18(3):452-64.
Lee, 2014, Accurate read mapping using a graph-based human pan-genome, ASHG 2014 Abstracts.
Lee, Bioinformatics analysis of alternative splicing, Brief Bioinf. 2005;6(1):23-33.
Lee, Generating consensus sequences from partial order multiple sequence alignment graphs. Bioinformatics. May 22, 2003;19(8):999-1008.
LeGault et al., Inference of alternative splicing from RNA-Seq data with probabilistic splice graphs. Bioinformatics. Jul. 11, 2013;29(18):2300-10.
LeGault, 2010, Learning Probalistic Splice Graphs from RNA-Seq data, pages.cs.wisc.edu/~legault/cs760_writeup.pdf; retrieved from the internet on Apr. 6, 2014.
Leipzig et al., The Alternative Splicing Gallery (ASG): bridging the gap between genome and transcriptome. Nucleic Acids Research. Jan. 1, 2004;32(13):3977-83.
Li et al., A survey of sequence alignment algorithms for next-generation sequencing. Briefings in bioinformatics. Sep. 1, 2010;11(5):473-83.
Li et al., Automated manipulation of systems biology models using libSBML within Taverna workflows. Bioinformatics. Dec. 1, 2007;24(2):287-9.
Li et al., Fast and accurate short read alignment with Burrows-Wheeler transform. bioinformatics. Jul. 15, 2009;25(14):1754-60.
Li et al., Performing statistical analyses on quantitative data in Taverna workflows: an example using R and maxdBrowse to identify differentially-expressed genes from microarray data. BMC bioinformatics. Dec. 2008;9(1):334.
Li et al., SOAP: short oligonucleotide alignment program. Bioinformatics. Jan. 28, 2008;24(5):713-4.
Li et al., SOAP2: an improved ultrafast tool for short read alignment. Bioinformatics. Jun. 3, 2009;25(15):1966-7.
Li et al., The sequence alignment/map format and SAMtools. Bioinformatics. Aug. 15, 2009;25(16):2078-9.
Li et al., TreeFam: a curated database of phylogenetic trees of animal gene families. Nucleic acids research. Jan. 1, 2006;34(suppl_1):D572-80.
Li, BGT: efficient and flexible genotype query across many samples. Bioinformatics. arXiv:1506.08452 [q-bio.GN]. Bioinformatics. 2015;32(4):590-2.
Li, Towards Better Understanding of Artificats in Variant Calling from High-Coverage Samples. Bioinformatics. arXiv:1404.0929 [q-bio.GN]. 2015. 8 pages.
Life Technologies, 2013, Rapid Exome Sequencing Using the Ion Proton System and Ion Ampliseq Technology, Application Note (5 Pages).
Lindgreen, AdapterRemoval: easy cleaning of next-generation sequencing reads. BMC research notes. Dec. 2012;5(1):337.
Lipman et al., Rapid and sensitive protein similarity searches. Science. Mar. 22, 1985;227(4693):1435-41.

(56) References Cited

OTHER PUBLICATIONS

Lücking et al., PICS-Ord: unlimited coding of ambiguous regions by pairwise identity and cost scores ordination. BMC bioinformatics. Dec. 2011;12(1):10.
Lupski et al., Genomic disorders: molecular mechanisms for rearrangements and conveyed phenotypes. PLoS genetics. Dec. 30, 2005;1(6):e49.
Ma et al., Multiple genome alignment based on longest path in directed acyclic graphs. International journal of bioinformatics research and applications. Oct. 1, 2010;6(4):366-83.
Machine translation of KR 10-1282798 B1 generated on Jan. 6, 2016, by the website of the European Patent Office (23 pages).
Machine translation produced on Jun. 1, 2015, by Espacenet of WO 2010/010992 A1 (11 pages).
Machine translation produced on Jun. 1, 2015, by WPIO website of WO 2013/035904 (10 pages).
Mamoulis, 2004, Non-contiguous sequence pattern queries, in Advances in Database Technology—EDBT 2004: 9th International Conference on Extending Database Technology, Heraklion, Crete, Greece, Mar. 14-18, 2004, Proceedings (18 pages); retreived from the internet on Jun. 3, 2016, at <http://Lcs.hku.hk/~nikos/seqjoin.pdf>.
Manolio, Genomewide association studies and assessment of the risk of disease. New England journal of medicine. Jul. 8, 2010;363(2):166-76.
Mardis, The $1,000 genome, the $100,000 analysis?, Genome Med. 2010;2:84-85.
Margulies et al., Genome sequencing in microfabricated high-density picolitre reactors. Nature. Sep. 2005;437(7057):376-380.
Marth et al., A general approach to single-nucleotide polymorphism discovery. Nature genetics. Dec. 1999;23(4):452.
Mazrouee et al., FastHap: fast and accurate single individual haplotype reconstruction using fuzzy conflict graphs. Bioinformatics. Aug. 22, 2014;30(17):i371-8.
McKenna et al., The Genome Analysis Toolkit: a MapReduce framework for analyzing next-generation DNA sequencing data. Genome research. Sep. 1, 2010;20(9):1297-303.
McSherry, Spectral partitioning of random graphs. InProceedings 42nd IEEE Symposium on Foundations of Computer Science Oct. 8, 2001 (pp. 529-537). IEEE.
Miller et al., Assembly algorithms for next-generation sequencing data. Genomics. Jun. 1, 2010;95(6):315-27.
Misra et al., Anatomy of a hash-based long read sequence mapping algorithm for next generation DNA sequencing. Bioinformatics. Nov. 18, 2010;27(2):189-95.
Missier, 2010, Taverna, reloaded, Proc. Scientific and Statistical Database Management, 22nd Int Conf, Heidelberg, Germany, Jun./Jul. 2010, Gertz & Ludascher, Eds., Springer.
Moudrianakis et al., Base sequence determination in nucleic acids with the electron microscope, III. Chemistry and microscopy of guanine-labeled DNA. Proceedings of the National Academy of Sciences of the United States of America. Mar. 1965;53(3):564-71.
Mount, Multiple Sequence Alignment, Bioinformatics, 2001, Cold Spring Harbor Laboratory Press, Cold Spring Harbor, New York. 2001; pp. 139-204.
Mourad et al., A hierarchical Bayesian network approach for linkage disequilibrium modeling and data-dimensionality reduction prior to genome-wide association studies. BMC bioinformatics. Dec. 2011;12(1):16: 1-20.
Myers, The fragment assembly string graph. Bioinformatics. Jan. 1, 2005;21(suppl_2):ii79-85.
Nagalakshmi et al., RNA-Seq: a method for comprehensive transcriptome analysis. Current protocols in molecular biology. Jan. 2010;89(1):4-11.
Nagarajan, Sequence assembly demystified, Nat Rev. 2013;14:157-167.
Najafi et al., Fundamental Limits of Pooled-DNA Sequencing. arXiv preprint arXiv:1604.04735. Apr. 16, 2016.

Nakao et al., Large-scale analysis of human alternative protein isoforms: pattern classification and correlation with subcellular localization signals. Nucleic acids research. Jan. 1, 2005;33(8):2355-63.
Needleman et al., A general method applicable to the search for similarities in the amino acid sequence of two proteins. Journal of molecular biology. Mar. 28, 1970;48(3):443-53.
Nenadic, 2010, Nested Workflows, The Taverna Knowledge Blog, Dec. 13, 2010. Retrieved on Feb. 25, 2016 from http://taverna.knowledgeblog.org/2010/12/13/nested-workflows/.
Neumann, Efficient Generation and Execution of DAG-Structured Query Graphs. Doctoral Dissertation. Universitat Mannheim. 2005. 170 pages.
Newman et al., An ultrasensitive method for quantitating circulating tumor DNA with broad patient coverage. Nature medicine. May 2014;20(5):548: 1-11.
Newman, Community detection and graph partitioning. arXiv:1305.4974v1. EPL (Europhysics Letters). Aug. 9, 2013;103(2):28003.
Ning et al., SSAHA: a fast search method for large DNA databases. Genome research. Oct. 1, 2001;11(10):1725-9.
Oinn et al., Taverna: a tool for the composition and enactment of bioinformatics workflows. Bioinformatics. Jun. 17, 2004;20(17):3045-54.
Oinn et al., Taverna: lessons in creating a workflow environment for the life sciences. Concurrency and Computation: Practice and Experience. Aug. 25, 2006;18(10):1067-100.
Olsson et al., Serial monitoring of circulating tumor DNA in patients with primary breast cancer for detection of occult metastatic disease. EMBO molecular medicine. Aug. 1, 2015;7(8):1034-47.
O'Rawe et al., Low concordance of multiple variant-calling pipelines: practical implications for exome and genome sequencing. Genome medicine. Dec. 2013;5(3):28.
Oshlack et al., From RNA-seq reads to differential expression results. Genome biology. Dec. 2010;11(12):220.
Pabinger, A survey of tools for variant analysis of next-generation genome sequencing data, Brief Bioinf. 2013.
Parks et al., Detecting non-allelic homologous recombination from high-throughput sequencing data. Genome biology. Dec. 2015;16(1):72.
Paten et al., Cactus graphs for genome comparisons. Journal of Computational Biology. Mar. 1, 2011;18(3):469-81.
Paterson et al., An XML transfer schema for exchange of genomic and genetic mapping data: implementation as a web service in a Taverna workflow. BMC bioinformatics. Dec. 2009;10(1):252.
Pearson et al., Improved tools for biological sequence comparison. Proceedings of the National Academy of Sciences. Apr. 1, 1988;85(8):2444-8.
Pe'er et al., Evaluating and improving power in whole-genome association studies using fixed marker sets. Nature genetics. Jun. 2006;38(6):663-667.
Peixoto, Efficient Monte Carlo and greedy heuristic for the inference of stochastic block models. Physical Review E. Jan. 13, 2014;89(1):012804.
Pop et al., Comparative genome assembly. Briefings in bioinformatics. Sep. 1, 2004;5(3):237-48.
Pope et al., ROVER variant caller: read-pair overlap considerate variant-calling software applied to PCR-based massively parallel sequencing datasets. Source code for biology and medicine. Dec. 2014;9(1):3.
Popitsch et al., NGC: lossless and lossy compression of aligned high-throughput sequencing data. Nucleic Acids Research. 2012;41(1)e27:1-12.
Posada et al., Model test: testing the model of DNA substitution. Bioinformatics (Oxford, England). Jan. 1, 1998;14(9):817-8.
Potter et al., ASC: An associative-computing paradigm. Computer. Nov. 1994;27(11):19-25.
Potter, The ensemble analysis pipeline, Genome Res. 2004;14:934-941.
Pruesse et al., SINA: accurate high-throughput multiple sequence alignment of ribosomal RNA genes. Bioinformatics. May 3, 2012;28(14):1823-9.
Quail et al., A tale of three next generation sequencing platforms: comparison of Ion Torrent, Pacific Biosciences and Illumina MiSeq sequencers. BMC genomics. Dec. 2012;13(1):341.

(56) References Cited

OTHER PUBLICATIONS

Quast et al., The SILVA ribosomal RNA gene database project: improved data processing and web-based tools. Nucleic Acids Research. 2013;41:590-6.
Rajaram et al., Pearl millet [Pennisetum glaucum (L.) R. Br.] consensus linkage map constructed using four RIL mapping populations and newly developed EST-SSRs. BMC genomics. Dec. 2013;14(1):159.
Ramirez-Gonzalez et al., Gee Fu: a sequence version and web-services database tool for genomic assembly, genome feature and NGS data. Bioinformatics. Jul. 29, 2011;27(19):2754-5.
Raphael et al., A novel method for multiple alignment of sequences with repeated and shuffled elements. Genome Research. Nov. 1, 2004;14(11):2336-46.
Robertson et al., De novo assembly and analysis of RNA-seq data. Nature methods. Nov. 2010;7(11):909.
Rödelsperger et al., Syntenator: multiple gene order alignments with a gene-specific scoring function. Algorithms for Molecular Biology. Dec. 2008;3(1):14.
Rognes et al., Six-fold speed-up of Smith-Waterman sequence database searches using parallel processing on common microprocessors. Bioinformatics. Aug. 1, 2000;16(8):699-706.
Rognes, Faster Smith-Waterman database searches with inter-sequence SIMD parallelisation. BMC bioinformatics. Dec. 2011;12(1):221.
Rognes, ParAlign: a parallel sequence alignment algorithm for rapid and sensitive database searches. Nucleic acids research. Apr. 1, 2001;29(7):1647-52.
Ronquist et al., MrBayes 3.2: efficient Bayesian phylogenetic inference and model choice across a large model space. Systematic biology. May 1, 2012;61(3):539-42.
Rothberg et al., An integrated semiconductor device enabling non-optical genome sequencing. Nature. Jul. 2011;475(7356):348-352.
Saebo et al., PARALIGN: rapid and sensitive sequence similarity searches powered by parallel computing technology. Nucleic acids research. Jul. 1, 2005;33(suppl_2):W535-9.
Sato et al., Directed acyclic graph kernels for structural RNA analysis. BMC bioinformatics. Dec. 2008;9(1):318.
Schenk et al., A pipeline for comprehensive and automated processing of electron diffraction data in IPLT. Journal of structural biology. May 1, 2013;182(2):173-85.
Schmieder et al., Identification and removal of ribosomal RNA sequences from metatranscriptomes. Bioinformatics. 2012;28(3):433-5.
Schneeberger et al., Simultaneous alignment of short reads against multiple genomes. Genome biology. Sep. 2009;10(9):R98.2-R98.12.
Schwikowski et al., Weighted sequence graphs: boosting iterated dynamic programming using locally suboptimal solutions. Discrete Applied Mathematics. Apr. 1, 2003;127(1):95-117.
Shao et al., Bioinformatic analysis of exon repetition, exon scrambling and trans-splicing in humans. Bioinformatics. Nov. 24, 2005;22(6):692-8.
Sievers et al., Fast, scalable generation of high-quality protein multiple sequence alignments using Clustal Omega. Molecular systems biology. Jan. 1, 2011;7(1):539.
Slater et al., Automated generation of heuristics for biological sequence comparison. BMC bioinformatics. Dec. 2005;6(1):31.
Smith et al., Identification of common molecular subsequences. Journal of molecular biology. Mar. 25, 1981;147(1):195-7.
Smith et al., Multiple insert size paired-end sequencing for deconvolution of complex transcriptomes. RNA biology. May 1, 2012;9(5):596-609.
Soni et al., Progress toward ultrafast DNA sequencing using solid-state nanopores. Clinical chemistry. Nov. 1, 2007;53(11):1996-2001.
Sosa et al., Next-generation sequencing of human mitochondrial reference genomes uncovers high heteroplasmy frequency. PLoS computational biology. Oct. 25, 2012;8(10):e1002737.
Sroka et al., A formal semantics for the Taverna 2 workflow model. Journal of Computer and System Sciences. Sep. 1, 2010;76(6):490-508.
Sroka et al., CalcTav—integration of a spreadsheet and Taverna workbench. Bioinformatics. Jul. 19, 2011;27(18):2618-9.
Sroka et al., XQTav: an XQuery processor for Taverna environment. Bioinformatics. Mar. 21, 2006;22(10):1280-1.
Standish, Data structures, algorithms & software principles in C. Addison-Wesley Publishing Company. 1994:15 pages.
Standish, Data Structures, Algorithms and Software Principles in C. Chapter 10 Section 10.1: Introduction and Motivation and Section 10.2: Basic Concepts and Terminology. Addison-Wesley Publishing Company. 1995:405-411.
Stephens et al., A new statistical method for haplotype reconstruction from population data. The American Journal of Human Genetics. Apr. 1, 2001;68(4):978-89.
Stewart et al., A comprehensive map of mobile element insertion polymorphisms in humans. PLoS genetics. Aug. 18, 2011;7(8):e1002236.
Sturgeon et al., Rcda: A highly sensitive and specific alternatively spliced transcript assembly tool featuring upstream consecutive exon structures. Genomics. Dec. 1, 2012;100(6):357-62.
Subramanian et al., DIALIGN-TX: greedy and progressive approaches for segment-based multiple sequence alignment. Algorithms for Molecular Biology. Dec. 2008;3(1):1-11.
Sudmant et al., An integrated map of structural variation in 2,504 human genomes. Nature. Oct. 2015;526(7571):75-81.
Sun, Pairwise comparison between genomic sequences and optical-maps (Doctoral dissertation, New York University, Graduate School of Arts and Science, 131 pages); retreived from the internet on Jun. 3, 2016, at <https://cs.nyu.edu/mishra/PEOPLE/sun_bing.pdf>.
Szalkowski et al., Graph-based modeling of tandem repeats improves global multiple sequence alignment. Nucleic acids research. Jul. 22, 2013;41(17):e162.
Szalkowski, Fast and robust multiple sequence alignment with phylogeny-aware gap placement. BMC bioinformatics. Dec. 2012;13(1):129.
Tan et al., A comparison of using Taverna and BPEL in building scientific workflows: the case of caGrid. Concurrency and Computation: Practice and Experience. Jun. 25, 2010;22(9):1098-117.
Tan et al., CaGrid Workflow Toolkit: A taverna based workflow tool for cancer grid. BMC bioinformatics. Dec. 2010;11(1):542.
Tarhio et al., Approximate boyer-moore string matching. SIAM Journal on Computing. Apr. 1993;22(2):243-60.
Tewhey et al., The importance of phase information for human genomics. Nat Rev Genet. Mar. 2011;12(3):215-23. doi: 10.1038/nrg2950. Epub Feb. 8, 2011.
Thomas, Community-wide effort aims to better represent variation in human reference genome, Genome Web. 2014; (11 pages).
Torri et al., Next generation sequence analysis and computational genomics using graphical pipeline workflows. Genes. Aug. 30, 2012;3(3):545-75.
Trapnell et al., TopHat: discovering splice junctions with RNA-Seq. Bioinformatics. May 1, 2009;25(9):1105-11.
Trapnell et al., Transcript assembly and abundance estimation from RNA-Seq reveals thousands of new transcripts and switching among isoforms. Nature biotechnology. May 2010;28(5):511-515.
Trapnell, 2010, Transcript assembly and quantification by RNA-Seq reveals unannotated trancripts and isoform switching during cell differentiation, Nat Biolech 28(5):511-515.
Truszkowski et al., New developments on the cheminformatics open workflow environment CDK-Taverna. Journal of cheminformatics. Dec. 2011;3(1):54.
Turi et al., Taverna workflows: Syntax and semantics. In Third IEEE International Conference on e-Science and Grid Computing (e-Science 2007) Dec. 10, 2007 (pp. 441-448). IEEE.
Uchiyama et al., CGAT: a comparative genome analysis tool for visualizing alignments in the analysis of complex evolutionary changes between closely related genomes. BMC bioinformatics. Dec. 2006;7(1):472.
Wajid et al., Review of General Algorithmic Features for Genome Assembles for Next Generation Sequencers. Genomics Proteomics and Bioinformatics. Science Direct. Elsevier. 2012;10:58-73.

(56) References Cited

OTHER PUBLICATIONS

Wallace et al., Multiple sequence alignments. Current opinion in structural biology. Jun. 1, 2005;15(3):261-6.
Wang et al., Next generation sequencing has lower sequence coverage and poorer SNP-detection capability in the regulatory regions. Scientific reports. Aug. 5, 2011;1:55.
Wang et al., RNA-Seq: a revolutionary tool for transcriptomics. Nature reviews genetics. Jan. 2009;10(1):57-63.
Wassink et al., Using R in Taverna: RShell v1. 2. BMC research notes. Dec. 2009;2(1):138.
Waterman et al., Some biological sequence metrics. Advances in Mathematics. Jun. 1, 1976;20(3):367-87.
Wheeler et al., The complete genome of an individual by massively parallel DNA sequencing. Nature. Letters. 2008;452:872-6.
Wolstencroft et al., The Taverna workflow suite: designing and executing workflows of Web Services on the desktop, web or in the cloud. Nucleic acids research. May 2, 2013;41(W1):W556-61.
Wolstencroft K, Oinn T, Goble C, Ferris J, Wroe C, Lord P, Glover K, Stevens R. Panoply of utilities in Taverna. In First International Conference on e-Science and Grid Computing (e-Science'05) Jul. 5, 2005 (pp. 7-pp). IEEE. 156-162.
Wu et al., Fast and SNP-tolerant detection of complex variants and splicing in short reads. Bioinformatics. Feb. 10, 2010;26(7):873-81.
Xing et al., An expectation-maximization algorithm for probabilistic reconstructions of full-length isoforms from splice graphs. Nucleic acids research. Jan. 1, 2006;34(10):3150-60.
Yang et al., Community detection in networks with node attributes. In2013 IEEE 13th International Conference on Data Mining Dec. 7, 2013 (pp. 1151-1156). IEEE. arXiv:1401.7267.
Yang et al., Leveraging reads that span multiple single nucleotide polymorphisms for haplotype inference from sequencing data. Bioinformatics. Jul. 3, 2013;29(18):2245-52.
Yanovsky et al., Read mapping algorithms for single molecule sequencing data. InInternational Workshop on Algorithms in Bioinformatics Sep. 15, 2008 (pp. 38-49). Springer, Berlin, Heidelberg.
Yildiz et al., BIFI: a Taverna plugin for a simplified and user-friendly workflow platform. BMC research notes. Dec. 2014;7(1):740.
Yu et al., A tool for creating and parallelizing bioinformatics pipelines. In2007 DoD High Performance Computing Modernization Program Users Group Conference Jun. 18, 2007 (pp. 417-420). IEEE.
Yu et al., The construction of a tetraploid cotton genome wide comprehensive reference map. Genomics. Apr. 1, 2010;95(4):230-40.
Zeng et al., PyroHMMvar: a sensitive and accurate method to call short indels and SNPs for Ion Torrent and 454 data. Bioinformatics. Aug. 31, 2013;29(22):2859-68.
Zhang et al., Construction of a high-density genetic map for sesame based on large scale marker development by specific length amplified fragment (SLAF) sequencing. BMC plant biology. Dec. 2013;13(1):141.
Zhang, Taverna Mobile: Taverna workllows on Android, EMBnet J. 2013;19(8):43-45.
Zhao et al., Why workflows break—Understanding and combating decay in Taverna workflows. 2012 IEEE 8th International Conference on E-Science Oct. 8, 2012 (pp. 1-9). IEEE.
U.S. Appl. No. 18/132,353, filed Apr. 7, 2023, Locke et al.
U.S. Appl. No. 18/324,799, filed May 26, 2023, Locke et al.
PCT/US2014/061158, Feb. 4, 2015, International Search Report and Written Opinion.
PCT/US2014/058328, Dec. 30, 2014, International Search Report and Written Opinion.
PCT/US2014/061198, Feb. 4, 2015, International Search Report and Written Opinion.
PCT/US2014/061162, Mar. 19, 2015, International Search Report and Written Opinion.
PCT/US2016/057324, Jan. 10, 2017, International Search Report and Written Opinion.
PCT/US2016/036873, Sep. 7, 2016, International Search Report and Written Opinion.
PCT/US2014/061156, Feb. 17, 2015, International Search Report and Written Opinion.
PCT/US2014/052065, Dec. 11, 2014, International Search Report and Written Opinion.
PCT/US2014/052065, Feb. 23, 2016, International Search Report and Written Opinion.
PCT/US2014/060680, Jan. 27, 2015, International Search Report and Written Opinion.
PCT/US2014/060690, Feb. 10, 2015, International Search Report and Written Opinion.
PCT/US2015/010604, Mar. 31, 2015, International Search Report and Written Opinion.
PCT/US2015/015375, May 11, 2015, International Search Report and Written Opinion.
PCT/US2016/020899, May 5, 2016, International Search Report and Written Opinion.
PCT/US2017/013329, Apr. 7, 2017, International Search Report and Written Opinion.
PCT/US2017/012015, Apr. 19, 2017, International Search Report and Written Opinion.
PCT/US2017/018830, Aug. 31, 2017, International Search Report and Written Opinion.
PCT/US2015/054461, Jan. 5, 2016, International Search Report and Written Opinion.
PCT/US2015/048891, Nov. 17, 2015, International Search Report and Written Opinion.
PCT/US2016/033201, Sep. 2, 2016, International Search Report and Written Opinion.
EP14803268.3, Apr. 21, 2017, Communication pursuant to Article 94(3) EPC.
EP14837955.5, Mar. 29, 2017, Extended European Search Report and Written Opinion.
EP14847490.1, May 9, 2017, Extended European Search Report and Written Opinion.
EP14854801.9, Apr. 12, 2017, Extended European Search Report and Written Opinion.
SG11201601124Y, Mar. 1, 2018, Examination Report.
SG11201601124Y, Dec. 21, 2016, Written Opinion.
SG11201602903X, May 29, 2017, Written Opinion.
SG11201603039P, Jun. 12, 2017, Written Opinion.
SG11201603044S, Jul. 10, 2017, Written Opinion.
SG11201605506Q, Jun. 15, 2017, Written Opinion.

* cited by examiner

FIG. 7

SYSTEMS AND METHODS FOR EPIGENETIC ANALYSIS

CROSS-REFERENCE TO RELATED APPLICATIONS

This application claims the benefit under 35 U.S.C. § 120 and is a continuation of U.S. patent application Ser. No. 17/023,289, filed on Sep. 16, 2020, which is a continuation of U.S. application Ser. No. 15/007,874, filed Jan. 27, 2016, which claims priority to, and the benefit of, U.S. Provisional Application Ser. No. 62/209,058, filed Aug. 24, 2015, the contents of which are incorporated by reference.

TECHNICAL FIELD

The invention relates to epigenetic analysis.

BACKGROUND

Epigenetic modifications to the human genome are linked to cancer and other clinical pathologies. For example, hypomethylation of the genome is highly prevalent across all cancer types but also exhibits regional specificity depending on tumor type and stage as discussed in Hoffman, 2005, Causes and consequences of DNA hypomethylation in human cancer, Biochem Cell Biol 83(3):296-321. Epigenetic modifications are also thought to irreversibly alter the expression of genes during the normal differentiation of embryonic stem cells into specific tissues. Patterns of epigenetic modifications can potentially reveal such conditions as fetal chromosome disorders. See Hultén et al., 2011. Non-invasive prenatal diagnosis: An epigenetic approach to the detection of common fetal chromosome disorders by analysis of maternal blood samples, in Circulating Nucleic Acids in Plasma and Serum. Proc 6 Int Conf CNIPS, pp. 133-142, Gahan, Ed. Springer.

Unfortunately, existing approaches to studying patterns of epigenetic modification are limited. It is proposed that methylated cytosine in genomic DNA can be detected by bisulfite sequencing. Treatment of DNA with bisulfite converts un-methylated cytosines to uracil without affecting methylated cytosines in the manner shown in FIG. 9. During subsequent amplification and sequencing steps, the uracil residues act as templates for incorporate of adenines, which implies that where sequencing yields a cytosine base call, it can be supposed that the original DNA included a methylated cytosine at that location. However, the sequencing procedures will yield adenine base calls for both the original thymines and the original unmethylated cytosines.

SUMMARY

The invention provides systems and methods for determining patterns of modification to a genome of a subject by representing the genome using a graph, such as a directed acyclic graph (DAG), with divergent paths for regions that are potentially subject to modification, profiling segments of the genome for evidence of epigenetic modification, and aligning the profiled segments to the DAG to determine locations and patterns of the epigenetic modification within the genome. The DAG can be created by sequencing at least a portion of the genome. To determine a pattern of methylation in the genome, segments can be profiled by a bisulfite sequencing, or Methyl-Seq, operation to produce a sequence in which a C represents a methylated cytosine in the original genome. That sequence can be aligned to the DAG to determine the pattern of methylation in the genome. Thus by determining the presence of methylated bases via the bisulfite sequencing operation, and determining the location of those bases in the genome by reference to the DAG, the invention may be used to provide a report that describes a pattern of epigenetic modification within the subject's genome. Since the DAG includes diverging paths for loci that are potentially modified, the sequence that profiles modification within a segment of the genome will align to the DAG. If the potentially modified residue was in-fact modified, then it will align to one of the diverging branches and if that residue was not modified it will align to the other of the diverging branches. Thus, use of a DAG allows for sensitive and accurate determinations of the locations—and therefore patterns—of epigenetic modification. The described method can be used to show a pattern of methylation across a substantial portion of gene, operon, chromosome, or genome. Thus methods of the invention can be used to provide valuable insights into an organism's development or a subject's health and can potentially reveal hypomethylation or other patterns of modification that may give an early warning of cancer or other clinically significant issues.

In certain aspects, the invention provides a method for determining genomic modifications in a subject. The method includes obtaining a sequence of nucleotide bases from nucleic acid from a subject and transforming the sequence into a graph. The graph is composed of vertices connected by edges and includes at least one path that splits into a first branch and a second branch, wherein the first branch represents a base observed in a position of the sequence and the second branch represents an alternative base not observed in the position. The first branch and the second branch may subsequently rejoin, e.g., just 3' to the position. A second sequence is obtained from bisulfite-treated nucleic acid from the subject and the method further includes determining an optimal alignment between the second sequence and the graph and observing—in a position in the second sequence that aligns to the position in the sequence—a corresponding base that matches the base observed in the position. The second sequence of nucleotide bases may be obtained by treating a portion of the nucleic acid from the subject with bisulfite and sequencing the bisulfite-treated nucleic acid from the subject. A report is provided that identifies a modified base at the position within the genome of the subject.

In some embodiments, the treatment selectively converts unmodified versions of the base to another nucleotide base. For example, the second sequence can be obtained from bisulfite-treated DNA from the subject. In certain embodiments, the base represented by the first branch of the graph is cytosine and the alternative base represented by the second branch is thymine, and the report identifies a methylated cytosine at the position within an exon, gene, operon, genome, or other segment of interest from the subject. Methods may include identifying methylated cytosines at a plurality of positions within the genome of the subject. In some embodiments, methods include identifying all other instances of the modified base occurring across at least 50% of a length of a chromosome of the genome of the subject. The report may identify an unmodified version of the base at a different position in the genome of the subject (e.g., the report may show what is and is not modified across a gene, operon, chromosome, or genome). The sequence and the second sequence may be derived from sequence reads generated by operating a nucleic acid sequencing instrument.

Preferably the steps are performed using a computer system comprising a processor coupled to a memory subsystem, and the graph is stored in the memory subsystem using adjacency lists. In some embodiments, there is an adjacency list for each vertex and edge, in which the adjacency list for a vertex or edge lists the edges or vertices to which that vertex or edge is adjacent. Each entry in the adjacency list is a pointer to the adjacent vertex or edge. Preferably, each pointer identifies a physical location in the memory subsystem at which the adjacent object is stored.

Methods of the invention may use an iterative process to accommodate treatment procedures that do not always treat each and every modified base. For example, where some given bisulfite treatment does not always convert every methylated cytosine, the method may include performing a plurality of replicate bisulfite treating, sequencing, and alignment operations and calling a methylated cytosine when a plurality of replicate sequences include a cytosine aligned to the position of the sequence.

Methods may be used to provide a report on phenomenon with clinical or developmental significance to a subject. For example, a report may identify a gene in the subject for which transcription has been regulated by the methylated cytosine at the position within the genome of the subject. In some embodiments, the report identifies a methylation status of a CpG island within the genome of the subject, for example, whether the CpG island is hyper- or hypo-methylated, or a pattern of methylation within the CpG island.

Aspects of the invention provide a computer system for determining genomic modifications in a subject. The computer system includes a processor coupled to a memory subsystem and is operable to obtain a sequence of nucleotide bases from nucleic acid from a subject and transform the sequence into a graph. The graph includes vertices connected by edges and at least one path that splits into a first branch and a second branch, wherein the first branch represents a base observed in a position of the sequence and the second branch represents an alternative base not observed in the position. The first branch and the second branch may subsequently rejoin, e.g., just 3' to the position. The graph is preferably stored in the memory subsystem using adjacency lists. In some embodiments, there is an adjacency list for each vertex and edge, in which the adjacency list for a vertex or edge lists the edges or vertices to which that vertex or edge is adjacent. Each entry in adjacency list is a pointer to the adjacent vertex or edge. Preferably, each pointer identifies a physical location in the memory subsystem at which the adjacent object is stored. The system may be operated to obtain a second sequence from bisulfite-treated nucleic acid from the subject and determine an optimal alignment between the second sequence and the graph. The system is operable to observe—in a position in the second sequence that aligns to the position in the sequence—a corresponding base that matches the base observed in the position. The system provides a report that identifies a modified base at the position within the genome of the subject.

In some embodiments, the treatment selectively converts unmodified versions of the base to another nucleotide base. In certain embodiments, the base represented by the first branch of the graph is cytosine and the alternative base represented by the second branch is thymine, and the report identifies a methylated cytosine at the position within the genome of the subject. In certain embodiments, the system is operable to identify methylated cytosines at a plurality of positions within the genome of the subject. In some embodiments, the system identifies all other instances of the modified base occurring across at least 50% of a length of a chromosome of the genome of the subject. The report may identify an unmodified version of the base at a different position in the genome of the subject (e.g., the report may show what is and is not modified across a gene, operon, chromosome, or genome). The sequence and the second sequence may be derived from sequence reads generated by operating a nucleic acid sequencing instrument.

The system may provide a report on phenomenon with clinical or developmental significance to a subject. For example, a report may identify a gene in the subject for which transcription has been regulated by the methylated cytosine at the position within the genome of the subject. In some embodiments, the report identifies a methylation status of a CpG island within the genome of the subject.

BRIEF DESCRIPTION OF THE DRAWINGS

FIG. 7 shows the matrices used by a modified Smith-Waterman operation for performing an alignment against a graph.

DETAILED DESCRIPTION

The invention provides systems and methods for the graph-based analysis of epigenetic phenomenon. Systems and methods of the invention may be used with Methyl-Seq data to profile patterns of epigenetic modifications in a genome of a subject. The invention includes the insight that the complex and frequently-compromised data produced by Methyl-Seq sequencing is particularly well suited to benefit from the disclosed graph-based alignment methods. In certain embodiments, the invention uses a graph, such as a directed acyclic graph (DAG) to represent a genome or region thereof with potentially modified loci being included in the DAG in branches for each of the modified and unmodified forms. A technique such as Methyl-Seq can be used to profile a segment of the genome to identify modified residues, and the profiled segment can be compared to the DAG, using for example a modified Smith-Waterman operation to determine locations and patterns of the modified residues within the genome.

Figure 1:
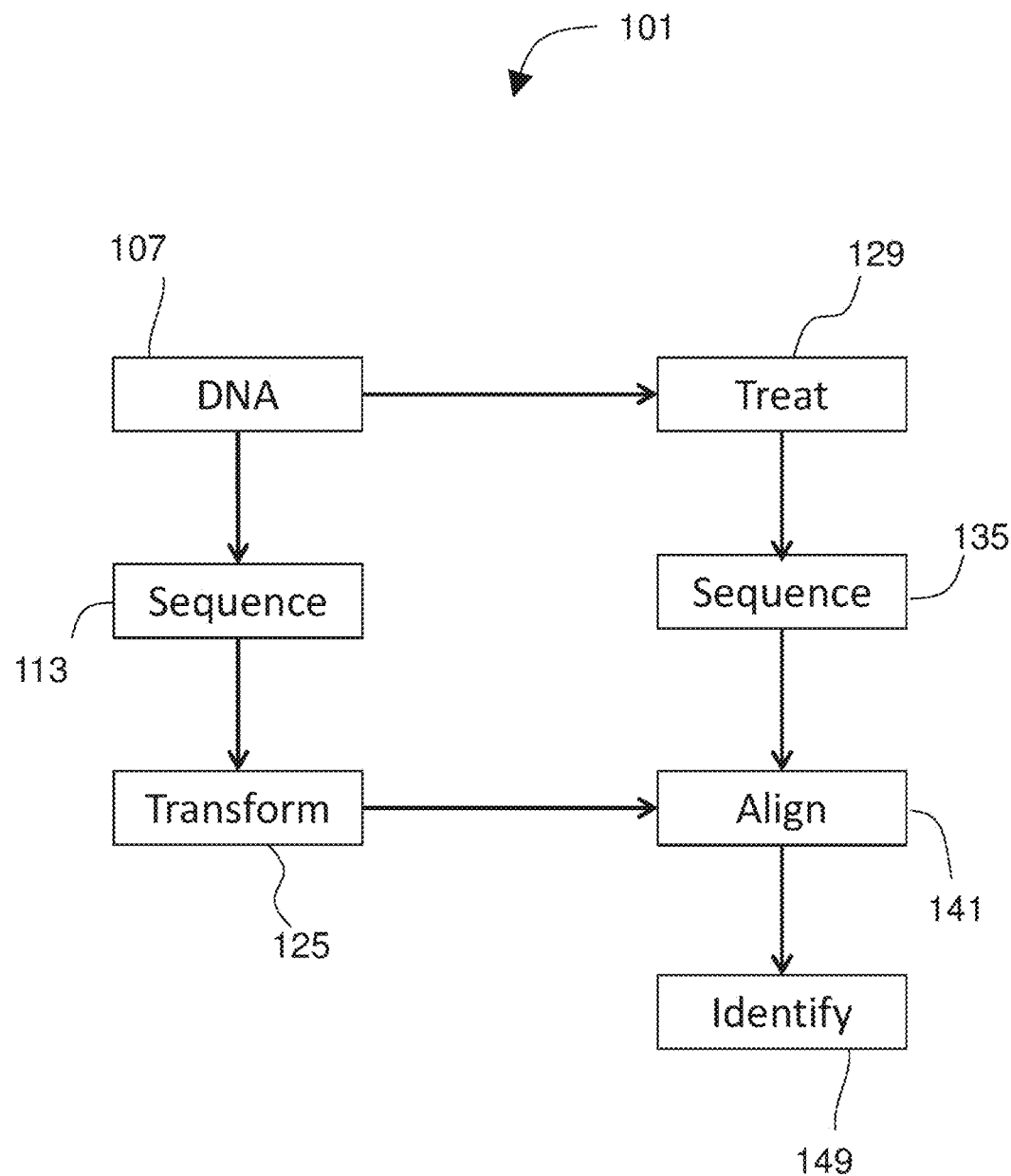
FIG. 1 diagrams a method for profiling epigenetic modifications in a genome.

FIG. 1 diagrams a method 101 for determining a pattern of epigenetic modifications in a genome. The method 101 includes obtaining a sequence 113 of nucleotide bases from nucleic acid 107 from a subject and transforming 125 the sequence into a graph. The graph is composed of vertices connected by edges and includes at least one path that splits into a first branch and a second branch, wherein the first branch represents a base observed in a position of the sequence and the second branch represents an alternative base not observed in the position. The first branch and the second branch may subsequently rejoin, e.g., just 3' to the position. A second sequence 135 is obtained from bisulfite-treated nucleic acid 129 from the subject and the method further includes determining an optimal alignment 141 between the second sequence and the graph and observing 149—in a position in the second sequence that aligns to the position in the sequence—a corresponding base that matches the base observed in the position. A report is provided that identifies a modified base at the position within the genome of the subject.

Figure 2:
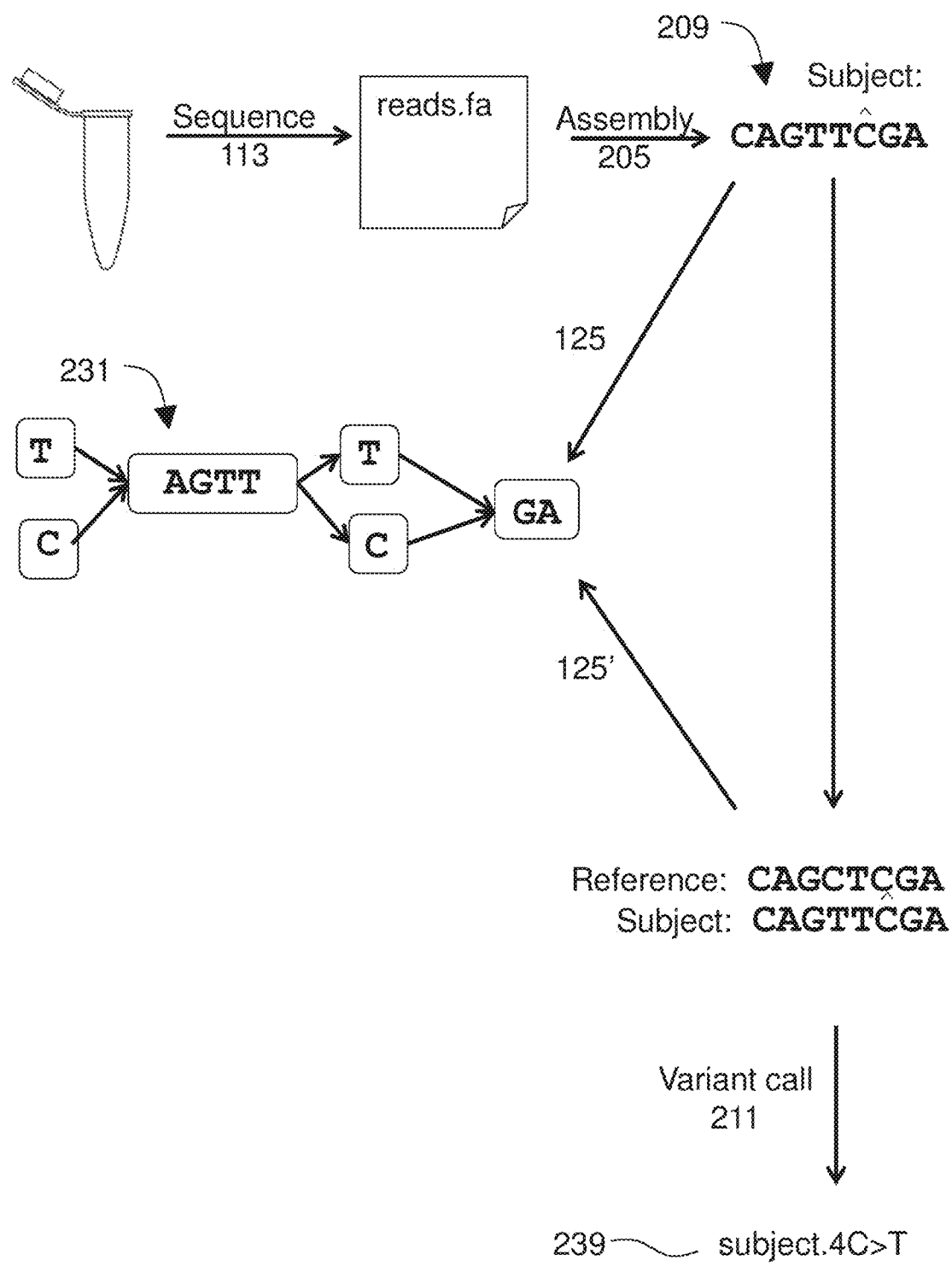
FIG. 2 illustrates transforming a sequence from a genome into a graph.

FIG. 2 illustrates obtaining 113 a sequence 209 from a genome of a subject and transforming 125 the sequence into a graph. FIG. 2 also shows that the obtained sequence 113 can be used in a variant calling operation 211.

In certain embodiments, sequence reads are obtained by performing sequencing on a sample from a subject. Sequencing may be by any method known in the art. See, generally, Quail, et al., 2012. A tale of three next generation sequencing platforms: comparison of Ion Torrent, Pacific Biosciences and Illumina MiSeq sequencers, BMC Genomics 13:341. DNA sequencing techniques include classic dideoxy sequencing reactions (Sanger method) using labeled terminators or primers and gel separation in slab or capillary, sequencing by synthesis using reversibly terminated labeled nucleotides, pyrosequencing. 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing.

A sequencing technique that can be used includes, for example, use of sequencing-by-synthesis systems sold under the trademarks GS JUNIOR, GS FLX+ and 454 SEQUENCING by 454 Life Sciences, a Roche company (Branford, CT), and described by Margulies, M. et al., Genome sequencing in micro-fabricated high-density picotiter reactors. Nature, 437:376-380 (2005); U.S. Pat. Nos. 5,583,024; 5,674,713; and 5,700,673, the contents of which are incorporated by reference herein in their entirety. 454 sequencing involves two steps. In the first step of those systems, DNA is sheared into blunt-end fragments attached to DNA capture beads and then amplified in droplets. In the second step, pyrosequencing is performed on each DNA fragment in parallel. Addition of one or more nucleotides generates a light signal that is recorded by a CCD camera in a sequencing instrument.

Another example of a DNA sequencing technique that can be used is SOLiD technology by Applied Biosystems from Life Technologies Corporation (Carlsbad, CA). In SOLiD sequencing, genomic DNA is sheared into fragments, and adaptors are attached to generate a fragment library. Clonal bead populations are prepared in microreactors containing beads, primers, template, and PCR components. Following PCR, the templates are denatured and enriched and the sequence is determined by a process that includes sequential hybridization and ligation of fluorescently labeled oligonucleotides.

Another example of a DNA sequencing technique that can be used is ion semiconductor sequencing using, for example, a system sold under the trademark ION TORRENT by Ion Torrent by Life Technologies (South San Francisco, CA). Ion semiconductor sequencing is described, for example, in Rothberg, et al., An integrated semiconductor device enabling non-optical genome sequencing, Nature 475:348-352 (2011); U.S. Pubs. 2009/0026082, 2009/0127589, 2010/0035252, 2010/0137143, 2010/0188073, 2010/0197507, 2010/0282617, 2010/0300559, 2010/0300895, 2010/0301398, and 2010/0304982, each incorporated by reference. DNA is fragmented and given amplification and sequencing adapter oligos. The fragments can be attached to a surface. Addition of one or more nucleotides releases a proton (H+), which signal is detected and recorded in a sequencing instrument.

Another example of a sequencing technology that can be used is Illumina sequencing. Illumina sequencing is based on the amplification of DNA on a solid surface using fold-back PCR and anchored primers. Genomic DNA is fragmented and attached to the surface of flow cell channels. Four fluorophore-labeled, reversibly terminating nucleotides are used to perform sequential sequencing. After nucleotide incorporation, a laser is used to excite the fluorophores, and an image is captured and the identity of the first base is recorded. Sequencing according to this technology is described in U.S. Pub. 2011/0009278, U.S. Pub. 2007/0114362, U.S. Pub. 2006/0024681, U.S. Pub. 2006/0292611, U.S. Pat. Nos. 7,960,120, 7,835,871, 7,232,656, 7,598,035, 6,306,597, 6,210,891, 6,828,100, 6,833,246, and 6,911,345, each incorporated by reference.

Other examples of a sequencing technology that can be used include the single molecule, real-time (SMRT) technology of Pacific Biosciences (Menlo Park. CA) and nanopore sequencing as described in Soni and Meller, 2007 Clin Chem 53:1996-2001.

As shown in FIG. 2, sequencing 113 generates a plurality of reads. Reads according to the invention generally include sequences of nucleotide data anywhere from tens to thousands of bases in length. Reads may be stored in any suitable format such as, for example, FASTA or FASTQ format. FASTA is originally a computer program for searching sequence databases and the name FASTA has come to also refer to a standard file format. See Pearson & Lipman, 1988, Improved tools for biological sequence comparison, PNAS 85:2444-2448. A sequence in FASTA format begins with a single-line description, followed by lines of sequence data. The description line is distinguished from the sequence data by a greater-than (">") symbol in the first column. FASTQ files are similar to FASTA but further include a line of quality scores. Typically, sequence reads will be obtained 105 in a format such as FASTA, FASTQ, or similar.

Obtaining the sequence 209 may include the assembly 205 of sequence reads. Sequence assembly 205 may include any suitable methods known in the art including de novo assembly, reference-guided assembly, others, or combinations thereof. In a preferred embodiment, sequence reads are assembled 205 using graph-based alignment methods. See, e.g., U.S. Pub. 2015/0057946 and U.S. Pub. 2015/0056613, both incorporated by reference. Embodiments of a graph and its use are discussed in greater detail below. The result of assembly 205 is a sequence 209 representing the corresponding portion of the subject's genome.

All individuals (except identical twins) are genetically unique. Accordingly, systems and methods of the invention may be used for variant calling 211 to produce genotype information 239 about un-modified bases in the subject's genome (i.e., those bases in the subject's genome which differ from a reference genome). Any suitable variant-calling operation can be performed and a variety of variant calling operations are known in the art. For example, where the organism is a person, variant calling can include aligning sequence reads to a reference such as a DAG or the human genome referred to as hg18 and reporting SNP alleles in a format such as a Sequence Alignment Map (SAM) or a Variant Call Format (VCF) file. In certain embodiments, reads are aligned to hg18 using Burrows-Wheeler Aligner version 0.5.7 for short alignments, and genotype calls are made using Genome Analysis Toolkit. See Li & Durbin, 2009, Fast and accurate short read alignment with Burrows-Wheeler Transform. Bioinformatics 25:1754-60 and McKenna et al., 2010, The Genome Analysis Toolkit: a MapReduce framework for analyzing next-generation DNA sequencing data, Genome Res 20(9):1297-1303, the contents of each of which are incorporated by reference. Alignment to hg18 and variant calling produces results ("variant calls") that may be stored as a sequence alignment map (SAM) or binary alignment map (BAM) file-comprising an alignment string (the SAM format is described, e.g., in Li, et al., The Sequence Alignment/Map format and SAMtools. Bioinformatics, 2009, 25(16):2078-9). Alignment strings known in the art include Simple UnGapped Alignment Report (SUGAR), Verbose Useful Labeled Gapped Alignment Report (VULGAR), and Compact Idiosyncratic Gapped Alignment Report (CIGAR) (Ning, Z., et al., Genome Research 11(10):1725-9 (2001)). These strings are implemented, for example, in the Exonerate sequence alignment software from the European Bioinformatics Institute (Hinxton, UK). CIGAR displays or includes gapped alignments one-per-line. CIGAR is a compressed pairwise alignment format reported as a CIGAR string. A CIGAR string is useful for representing long (e.g. genomic) pairwise alignments. A CIGAR string is used in SAM format to represent alignments of reads to a reference genome sequence. In a CIGAR string, each character is preceded by a number, giving the base counts of the event. Characters used can include M, I, D, N, and S (M=match; I=insertion; D=deletion; N=gap; S=substitution). The CIGAR string defines the sequence of matches/mismatches and deletions (or gaps). Additionally or alternatively, output from the variant calling may be provided in a variant call format (VCF) file. A typical VCF file 183 will include a header section and a data section. The header contains an arbitrary number of meta-information lines, each starting with characters '##', and a TAB delimited field definition line starting with a single '#' character. The field definition line names eight mandatory columns and the body section contains lines of data populating the columns defined by the field definition line. The VCF format is described in Danecek et al., 2011. The variant call format and VCFtools. Bioinformatics 27(15):2156-2158. Further discussion of methods for variant calling may be found in U.S. Pub. 2013/0073214; U.S. Pub. 2013/0345066; U.S. Pub. 2013/0311106; U.S. Pub. 2013/0059740; and U.S. Pub. 2012/0157322, the contents of each of which are incorporated by reference.

In a preferred embodiment, variant calling includes mapping the sequence to a reference graph, such as a directed acyclic graph (DAG) that represents known human genomic variation using methods and systems as described in U.S. Pub. 2015/0057946 and U.S. Pub. 2015/0056613, both incorporated by reference. Using alignment operations of the invention, reads can be rapidly mapped to a DAG despite their large numbers or short lengths. Numerous benefits obtain by using a DAG as a reference. For example, aligning against a DAG is more accurate than aligning against a linear reference and then attempting to adjust one's results in light of other extrinsic information. This is primarily because the latter approach enforces an unnatural asymmetry between the sequence used in the initial alignment and other information. Aligning against an object that potentially represents all the relevant physical possibilities is much more computationally efficient than attempting to align against a linear sequence for each physical possibility (the number of such possibilities will generally be exponential in the number of junctions). A modified Smith-Waterman operation for comparing a sequence to a reference DAG that may be used for variant calling is discussed in greater detail below. The optional variant calling 211 gives genotype information 239 about un-modified bases in the subject's genome.

For the epigenetic profiling, the sequence 209 is transformed 125 into a graph 231. As shown in FIG. 2, the graph 231 can be arrived at by transforming 125 the sequence 209 or by transforming 125' the sequence 209 after any alignment to a reference (be it a linear reference such as hg19 or a DAG as discussed above). For example, in certain embodiments, a subject's genotype information 239 (e.g., the set of variant bases in the subject's genome compared to the reference genome) may be incorporated into a graph. In these embodiments, new edges representing variation may be inserted into the graph (if not already present). In this way, the subject's genome is accounted for by the graph.

With continued reference to FIG. 2, it can be seen that a caret over a C is used within sequence 209 to represent what was a methylated cytosine within the original genome from the subject. At the stages of obtaining the sequence 209 and transforming the sequence 209 into the graph 231, it is not necessary to have any knowledge of the methylated cytosine and that mark is included in FIG. 2 to illustrate how systems and methods of the invention function.

In the depicted embodiment, the sequence 209 is transformed into the graph 231 (a "Methyl-Seq-ready graph") by creating nodes for sequence substrings and edges connecting the nodes. The graph may be created in the computer memory in that way or that relationship may be reversed with sequence stored in the edge objects. Creating the graph 231 further includes adding a single-nucleotide thymine branch as an alternative in place of every cytosine in sequence 209.

By allowing for the fact that cytosine may, post-bisulfite-treatment, be sequenced either as cytosine or thymine, using a graph here, pre-bisulfite treatment, is an excellent way to achieve unbiased and accurate alignment, and using a graph based on the subject's normal genome allows one to distinguish between C→T SNPs (which will show up as Ts in the alignment) from unmethylated cytosine nucleotides (which will only show up as Ts in the Methyl-Seq-based sequence). The latter point is important because in many cases the proportion of Cs methylated in a particular region will be the biologically-significant fact (e.g., will be the trigger for silencing a particular gene). As shown in FIG. 2, the variant calling 211 can provide genotype information 239 about un-modified bases in the subject's genome and thus, here, calls a genotype for the subject as g.4C>T (where the "4" would actually typically be distance from the beginning of the feature of interest (e.g., exon, gene, chromosome, etc). Regardless of the variant calling 211 operation, methods of the invention include transforming the sequence 209 into the graph 231 using a computer system with a memory subsystem storing the graph 231 in the memory subsystem.

Figure 3:
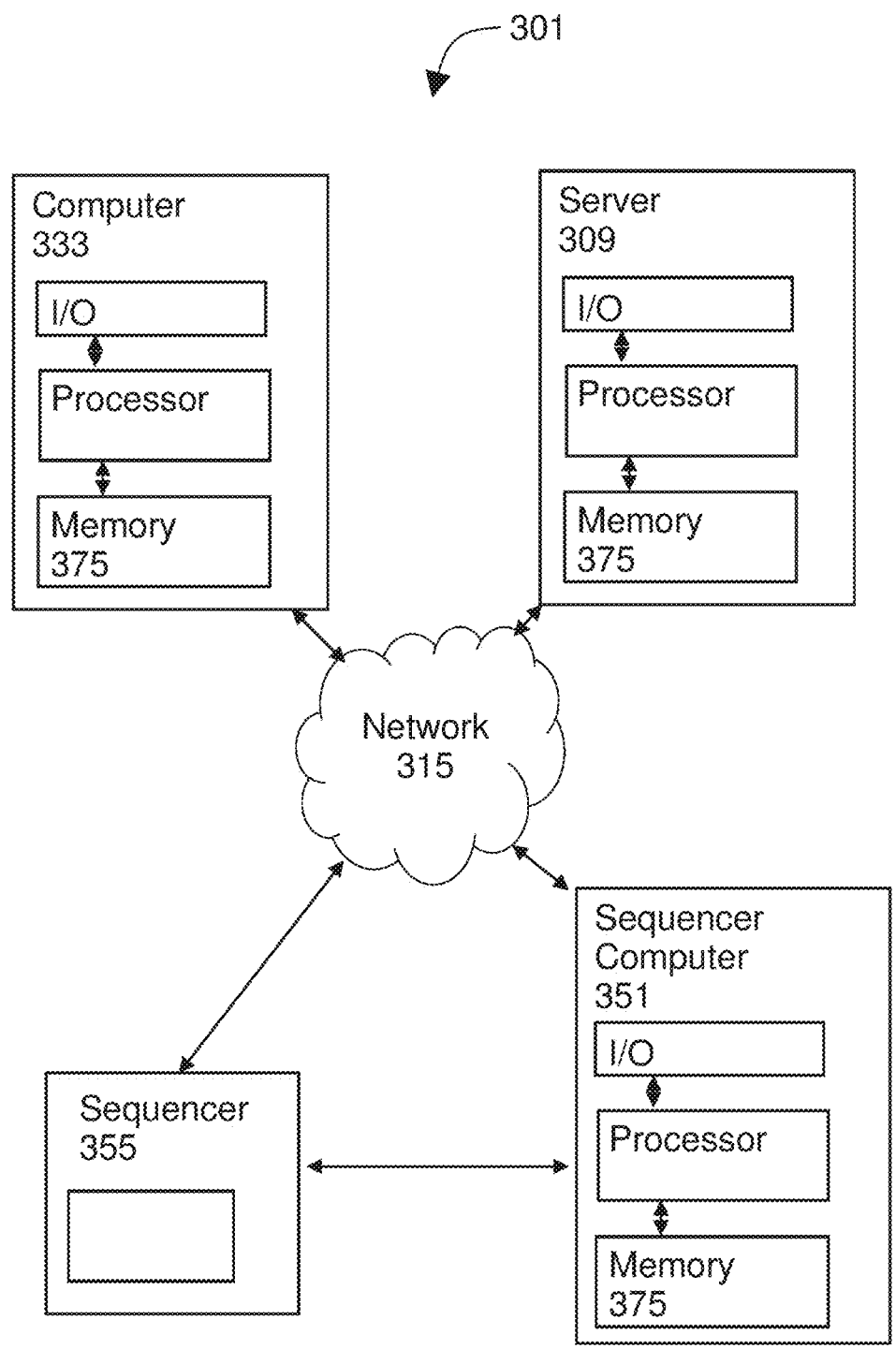
FIG. 3 illustrates a computer system for performing methods of the invention.

FIG. 3 illustrates a computer system 301 suitable for performing methods of the invention. The system 301 includes at least one computer 333. Optionally, the system 301 may further include one or more of a server computer 309 and a sequencer 355, which may be coupled to a sequencer computer 351. Each computer in the system 301 includes a processor coupled to a memory device and at least one input/output device. Thus the system 301 includes at least one processor coupled to a memory subsystem (e.g., a memory device or collection of memory devices 375). Using those mechanical components, the system 301 is operable to obtain a sequence generated by sequencing nucleic acid from a genome of a patient. The system uses the processor to transform the sequence 209 into the graph 231.

Processor refers to any device or system of devices that performs processing operations. A processor will generally include a chip, such as a single core or multi-core chip, to provide a central processing unit (CPU). A processor may be provided by a chip from Intel or AMD. A processor may be any suitable processor such as the microprocessor sold under the trademark XEON E7 by Intel (Santa Clara. CA) or the microprocessor sold under the trademark OPTERON 6200 by AMD (Sunnyvale. CA).

The memory subsystem 375 contains one or any combination of memory devices. A memory device is a mechanical device that stores data or instructions in a machine-readable format. Memory may include one or more sets of instructions (e.g., software) which, when executed by one or more of the processors of the disclosed computers can accomplish some or all of the methods or functions described herein. Preferably, each computer includes a non-transitory memory device such as a solid state drive, flash drive, disk drive, hard drive, subscriber identity module (SIM) card, secure digital card (SD card), micro SD card, or solid-state drive (SSD), optical and magnetic media, others, or a combination thereof.

Using the described components, the system 301 is operable to produce a report (such as the report 801 of FIG. 8, described below) and provide the report 801 to a user via an input/output device. An input/output device is a mechanism or system for transferring data into or out of a computer. Exemplary input/output devices include a video display unit (e.g., a liquid crystal display (LCD) or a cathode ray tube (CRT)), a printer, an alphanumeric input device (e.g., a keyboard), a cursor control device (e.g., a mouse), a disk drive unit, a speaker, a touchscreen, an accelerometer, a microphone, a cellular radio frequency antenna, and a network interface device, which can be, for example, a network interface card (NIC), Wi-Fi card, or cellular modem.

Preferably the graph 231 is stored in the memory subsystem using adjacency lists, which may include pointers to identify a physical location in the memory subsystem 375 where each vertex is stored. In a preferred embodiment, the graph 231 is stored in the memory subsystem 375 using adjacency lists. In some embodiments, there is an adjacency list for each vertex. For discussion of implementations see 'Chapter 4. Graphs' at pages 515-693 of Sedgewick and Wayne, 2011, Algorithms, 4th Ed., Pearson Education, Inc., Upper Saddle River NJ, 955 pages, the contents of which are incorporated by reference and within which pages 524-527 illustrate adjacency lists.

Figure 4:
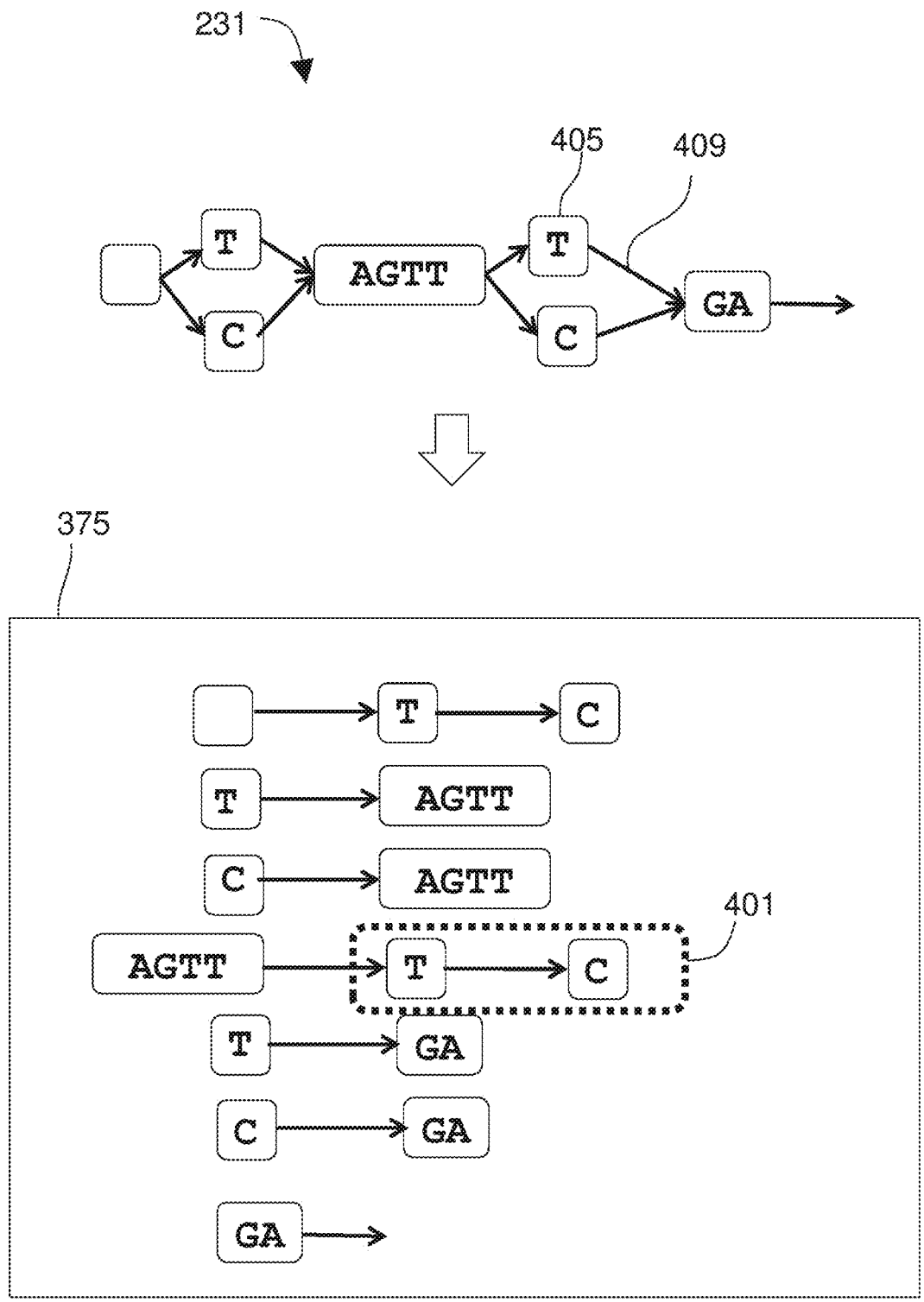
FIG. 4 shows the use of adjacency lists in an embodiment.

FIG. 4 shows the use of an adjacency list 401 for each vertex 405. The system uses the processor to create a graph that includes vertices and edges through the use of adjacency lists or index free adjacency. Thus, the processor may create the graph 231 using index-free adjacency wherein a vertex 405 includes a pointer to another vertex 405 to which it is connected and the pointer identifies a physical location in on a memory device where the connected vertex is stored. The graph 231 may be implemented using adjacency lists such that each vertex or edge stores a list of such objects that it is adjacent to. Each adjacency list comprises pointers to specific physical locations within a memory device for the adjacent objects.

In the top part of FIG. 4, the graph 231 is illustrated in a cartoon-like visual-friendly format. The graph 231 will typically be stored on a physical device of memory subsystem 375 in a fashion that provides for very rapid traversals.

In that sense, the bottom portion of FIG. 4 is not cartoon-like and represents that objects are stored at specific physical locations on a tangible part of the memory subsystem 375. Each node 405 is stored at a physical location, the location of which is in any adjacency list 401 that references that node. Each node 405 has an adjacency list 401 that includes every adjacent node in the graph 231. The entries in the list 401 are pointers to the adjacent nodes.

In certain embodiments, there is an adjacency list for each vertex and edge and the adjacency list for a vertex or edge lists the edges or vertices to which that vertex or edge is adjacent.

Figure 5:
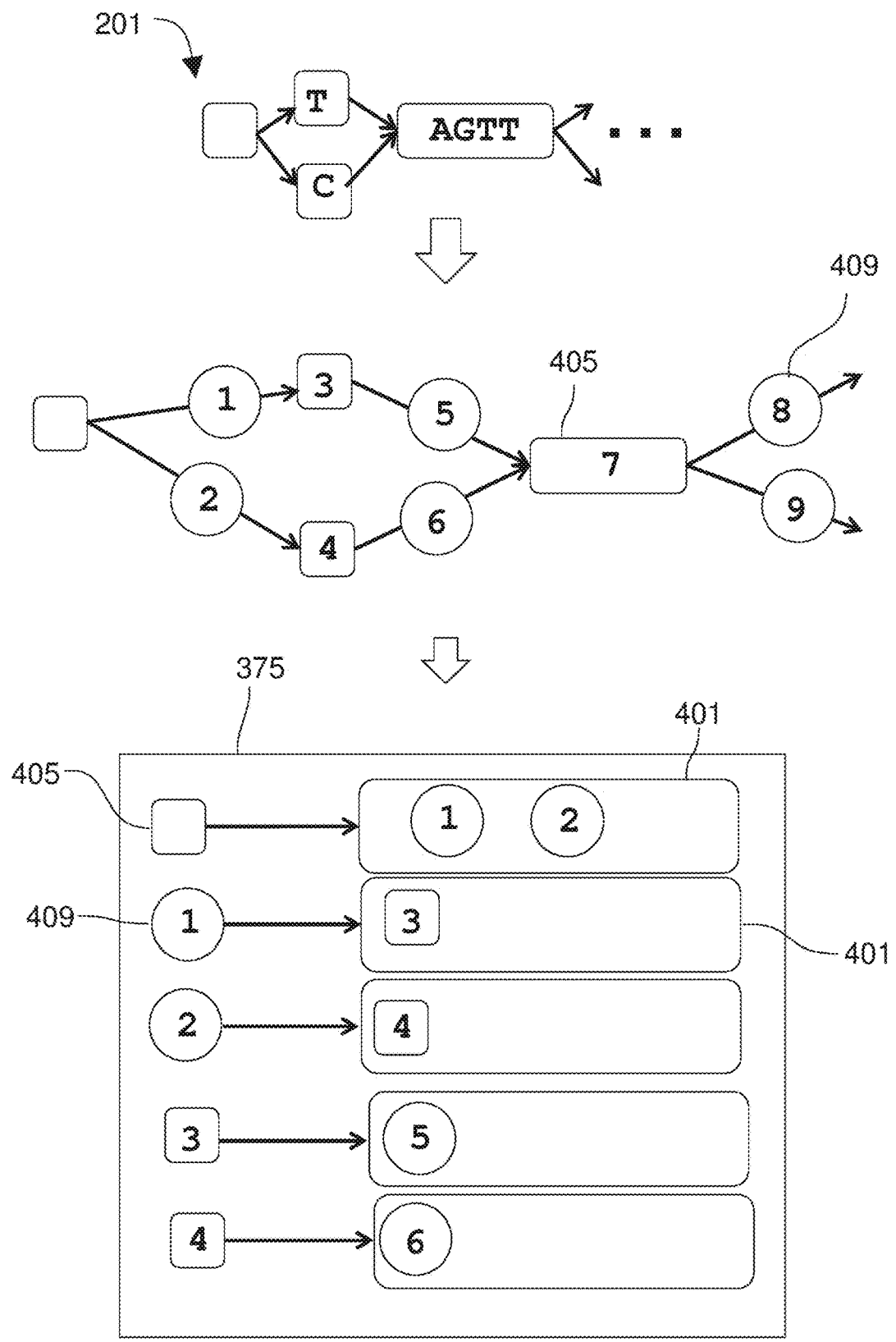
FIG. 5 shows the use of an adjacency list for each vertex and each edge of the graph.

FIG. 5 shows the use of an adjacency list 401 for each vertex 405 and edge 409. As shown in FIG. 5, system 301 creates the graph 231 using an adjacency list 401 for each vertex and edge, wherein the adjacency list 401 for a vertex 405 or edge 409 lists the edges or vertices to which that vertex or edge is adjacent. Each entry in adjacency list 401 is a pointer to the adjacent vertex or edge.

Preferably, each pointer identifies a physical location in the memory subsystem at which the adjacent object is stored. In the preferred embodiments, the pointer or native pointer is manipulatable as a memory address in that it points to a physical location on the memory but also dereferencing the pointer accesses intended data. That is, a pointer is a reference to a datum stored somewhere in memory; to obtain that datum is to dereference the pointer. The feature that separates pointers from other kinds of reference is that a pointer's value is interpreted as a memory address, at a low-level or hardware level. The speed and efficiency of the described graph genome engine allows sequence 209 to be queried against a genomic-scale genomic reference DAG (such as the DAG 231 of FIG. 2) containing millions of loci, using a computer system 301. Such a graph representation provides means for fast random access, modification, and data retrieval.

In some embodiments, fast random access is supported and graph object storage are implemented with index-free adjacency in that every element contains a direct pointer to its adjacent elements (e.g., as described in U.S. Pub. 2014/0280360 and U.S. Pub. 2014/0278590, incorporated by reference), which obviates the need for index look-ups, allowing traversals (e.g., as done in the modified SW alignment algorithm described herein) to be very rapid. Index-free adjacency is another example of low-level, or hardware-level, memory referencing for data retrieval (as required in alignment and as particularly pays off in terms of speed gains in the modified, multi-dimensional Smith-Waterman alignment described below). Specifically, index-free adjacency can be implemented such that the pointers contained within elements are in-fact references to a physical location in memory.

Since a technological implementation that uses physical memory addressing such as native pointers can access and use data in such a lightweight fashion without the requirement of separate index tables or other intervening lookup steps, the capabilities of a given computer, e.g., any modern consumer-grade desktop computer, are extended to allow for full operation of a genomic-scale DAG (i.e., a graph 231 that represents all loci in a substantial portion of the subject's genome). Thus storing graph elements (e.g., nodes and edges) using a library of objects with native pointers or other implementation that provides index-free adjacency—i.e., embodiments in which data is retrieved by dereferencing a pointer to a physical location in memory—actually improves the ability of the technology to provide storage, retrieval, and alignment for genomic information since it uses the physical memory of a computer in a particular way.

While no specific format is required for storage of a DAG, FIGS. 4 and 5 are presented to illustrate useful formats. In illustrations below, exemplary DAGs are presented and discussed as graphs, but it will be appreciated that a DAG qua graph can be translated directly to a data structure in computer memory or a text document and back.

With reference back to FIG. 1, methods include transforming 125 the sequence into a graph 231 and also obtaining 135 a second sequence from bisulfite-treated nucleic acid 129 from the subject aligning 141 the second sequence to the graph 231. In some embodiments, nucleic acid from the subject is treated 129 and sequenced 135 to obtain the second sequence.

Figure 6:
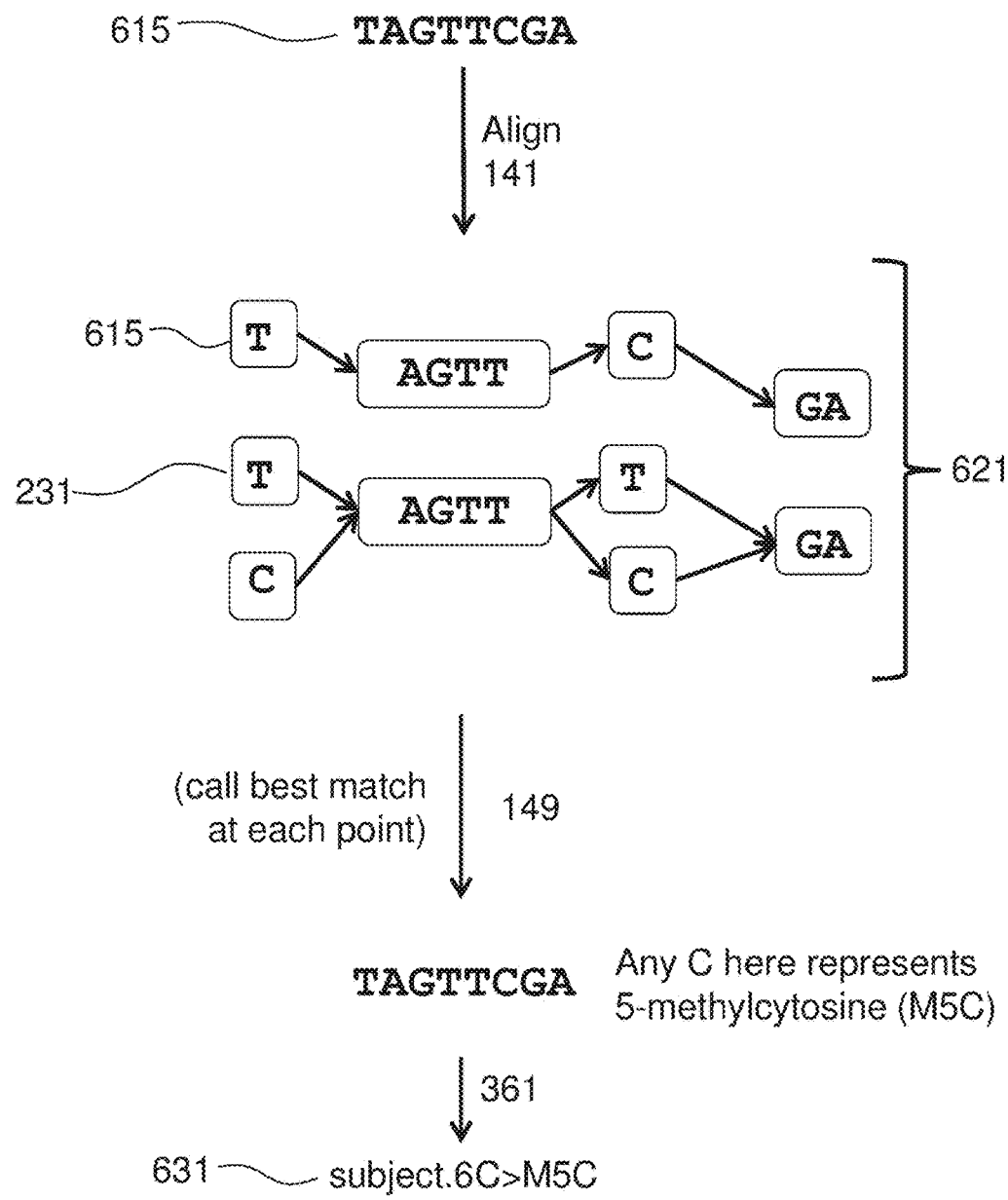
FIG. 6 diagrams obtaining the second sequence according to some embodiments.

FIG. 6 diagrams obtaining the second sequence according to some embodiments. FIG. 6 shows obtaining genomic DNA from a subject (e.g., blood sample, cultured cells, cultured bacteria, animal tissues etc.). The DNA may be isolated by using a commercially-available DNA extraction kit following the corresponding manufacturer's protocols.

In one embodiment, genomic DNA (1-10 μg) is dissolved in deionized water with 18 μl final volume. The DNA is denatured by boiling in a water bath for 20 min and adding 2 μl of 3 M NaOH and 380 μl 5 M sodium bisulfite solution. Mix, cover with mineral oil, incubate in dark at 50° C. for 12-16 h. Bisulfite treated DNA may purified using a Wizard DNA clean-up kit from Promega according to the manufacturer's protocol. The bisulfite-modified DNA is eluted in 50 μl deionized water and 11 μl 3 M NaOH is added. Incubate at 37° C. for 15 min to desulfonate the DNA. Add 166 μl 5 M ammonium acetate, 750 μl of absolute ethanol and 200 μl isopropanol to precipitate the DNA at −20° C. for 2-4 h. Centrifuge, wash with EtOH, and dry the DNA pellet. Re-suspend in TE or de-ionized water. Bisulfite PCR amplification can be performed as a regular PCR reaction. Prior to sequencing, purification of PCR products removes the residue of the PCR reaction that might interfere with the outcome of sequencing results. Commercially-available kits such as QIAquick PCR Purification Kit (Qiagen) can be used and the purified PCR products can be directly sequenced. If starting with single-molecules, it may be preferable to clone, e.g., using pGEM-T Easy vector system II (Promega), which provides a T4 DNA ligase system, a pGEM-T Easy vector and competent JM109 cells. Purified PCR products are ligated to the pGEM-T Easy vector and transformed into competent JM109 cells. The JM109 cells that carry the ligated vectors are selected on agar plates containing ampicillin/X-gal/IPTG by color and grown in LB medium. Plasmids containing the target DNA are extracted by using the QIAprep Spin Miniprep Kit (Qiagen) and subjected to standard sequencing analysis. All the procedures follow the manufacturer's protocol. For discussion see Li and Tollefsbol, 2011, DNA methylation detection: bisulfite genomic sequencing analysis, Methods Mol Biol 791:11-21; Li, 2007. Designing PCR primer for DNA methylation mapping. Methods Mol Biol 402:371-384; Li & Dahiya, 2002, MethPrimer: designing primers for methylation PCRs. Bioinformatics 18:1427-1431, the contents of each of which are incorporated by reference for all purposes. As shown in FIG. 6, methods of the invention may include sequencing 135 the bisulfite-treated DNA to produce the second sequence 615.

The second sequence 615 is aligned to the graph 231. This can include aligning the sequence reads produced by the sequencing 135 against the Methyl-Seq-ready graph 231 using, for example, a modified Smith-Waterman operation.

Performing the alignment 141 provides an optimal-scoring alignment 621. FIG. 6 shows a cartoon version of the second sequence 615 aligned to the graph 201. Making reference to the optimal scoring alignment 621, systems and methods of the invention may be used to observing 149—in a position in the second sequence 615 that aligns to the position in the sequence—a corresponding base that matches the base observed in the position. With continued reference to the alignment 621 illustrated in FIG. 6, it can be seen that the graph 231 includes two positions at which it splits into a first branch and a second branch, in which the first branch represents a base observed in a position of the sequence and the second branch represents an alternative base not observed in the position.

Using alignment 621 for example, systems and methods of the invention can be used to call 149 a methylated cytosine at any location in which C persists in the aligned sequence. To determine the optimal alignment 621, the sequence 615 may be aligned to the graph 621 using a modified Smith-Waterman operation that expands on the concept of a pairwise alignment.

Pairwise alignment generally involves placing one sequence along part of target, introducing gaps according to an algorithm, scoring how well the two sequences match, and preferably repeating for various position along the reference. The best-scoring match is deemed to be the alignment and represents an inference about what the sequence data represents. In some embodiments, scoring an alignment of a pair of nucleic acid sequences involves setting values for the probabilities of substitutions and indels. When individual bases are aligned, a match or mismatch contributes to the alignment score by a substitution probability, which could be, for example, 1 for a match and −0.33 for a mismatch. An indel deducts from an alignment score by a gap penalty, which could be, for example, −1. Gap penalties and substitution probabilities can be based on empirical knowledge or a priori assumptions about how sequences evolve. Their values affects the resulting alignment. Particularly, the relationship between the gap penalties and substitution probabilities influences whether substitutions or indels will be favored in the resulting alignment.

Stated formally, an alignment represents an inferred relationship between two sequences, x and y. For example, in some embodiments, an alignment A of sequences x and y maps x and y respectively to another two strings x' and y' that may contain spaces such that: (i) |x'|=|y'|; (ii) removing spaces from x' and y' should get back x and y, respectively; and (iii) for any i, x'[i] and y'[i] cannot be both spaces.

A gap is a maximal substring of contiguous spaces in either x' or y'. An alignment A can include the following three kinds of regions: (i) matched pair (e.g., x'[i]=y'[i]; (ii) mismatched pair, (e.g., x'[i]≠y'[i] and both are not spaces); or (iii) gap (e.g., either x'[i . . . j] or y'[i . . . j] is a gap). In certain embodiments, only a matched pair has a high positive score a. In some embodiments, a mismatched pair generally has a negative score b and a gap of length r also has a negative score g+rs where g, s<0. For DNA, one common scoring scheme (e.g. used by BLAST) makes score a=1, score b=−3, g=−5 and s=−2. The score of the alignment A is the sum of the scores for all matched pairs, mismatched pairs and gaps. The alignment score of x and y can be defined as the maximum score among all possible alignments of x and y.

Any pair may have a score a defined by a 4×4 matrix B of substitution probabilities. For example, $B(i,i)=1$ and $0 < B(i,j) < 1$ [for $i \neq j$] is one possible scoring system. For instance, where a transition is thought to be more biologically probable than a transversion, matrix B could include B(C,T)=0.7 and B(A,T)=0.3, or any other set of values desired or determined by methods known in the art.

Alignment according to some embodiments of the invention includes pairwise alignment. A pairwise alignment, generally, involves—for sequence Q (query) having m characters and a reference genome T (target) of n characters—finding and evaluating possible local alignments between Q and T. For any 1≤i≤n and 1≤j≤m, the largest possible alignment score of T[h . . . i] and Q[k . . . j], where h≤i and k≤j, is computed (i.e. the best alignment score of any substring of T ending at position i and any substring of Q ending at position j). This can include examining all substrings with cm characters, where c is a constant depending on a similarity model, and aligning each substring separately with Q. Each alignment is scored, and the alignment with the preferred score is accepted as the alignment. One of skill in the art will appreciate that there are exact and approximate algorithms for sequence alignment. Exact algorithms will find the highest scoring alignment, but can be computationally expensive. Two well-known exact algorithms are Needleman-Wunsch (J Mol Biol. 48(3):443-453, 1970) and Smith-Waterman (J Mol Biol. 147(1):195-197, 1981; Adv, in Math. 20(3), 367-387, 1976). A further improvement to Smith-Waterman by Gotoh (J Mol Biol, 162(3), 705-708, 1982) reduces the calculation time from O(m^2n) to O(mn) where m and n are the sequence sizes being compared and is more amendable to parallel processing. In the field of bioinformatics, it is Gotoh's modified algorithm that is often referred to as the Smith-Waterman algorithm. Smith-Waterman approaches are being used to align larger sequence sets against larger reference sequences as parallel computing resources become more widely and cheaply available. See, e.g., Amazon's cloud computing resources. All of the journal articles referenced herein are incorporated by reference in their entireties.

The original Smith-Waterman (SW) algorithm aligns linear sequences by rewarding overlap between bases in the sequences, and penalizing gaps between the sequences. Smith-Waterman also differs from Needleman-Wunsch, in that SW does not require the shorter sequence to span the string of letters describing the longer sequence. That is, SW does not assume that one sequence is a read of the entirety of the other sequence. Furthermore, because SW is not obligated to find an alignment that stretches across the entire length of the strings, a local alignment can begin and end anywhere within the two sequences.

The original SW algorithm is expressed for an n×m matrix H, representing the two strings of length n and m, in terms of equation (1):

$$H\_k0 = H\_01 = 0 (\text{for } 0 \le k \le n \text{ and } 0 \le l \le m)$$

$$H\_ij = \max\{H\_(i-1,j-1) + s(a\_i, b\_j), H\_(i-1,j) - W\_\text{in}, H\_(i,j-1) - W\_\text{del}, 0\}$$

$$(\text{for } 1 \le i \le n \text{ and } 1 \le j \le m) \quad (1)$$

In the equations above, s(ai,bj) represents either a match bonus (when ai=bj) or a mismatch penalty (when ai≠bj), and insertions and deletions are given the penalties Win and Wdel, respectively. In most instances, the resulting matrix has many elements that are zero. This representation makes it easier to backtrace from high-to-low, right-to-left in the matrix, thus identifying the alignment.

Once the matrix has been fully populated with scores, the SW algorithm performs a backtrack to determine the alignment. Starting with the maximum value in the matrix, the algorithm will backtrack based on which of the three values (Hi−1,j−1, Hi−1,j, or Hi,j−1) was used to compute the final maximum value for each cell. The backtracking stops when a zero is reached. The optimal-scoring alignment may contain greater than the minimum possible number of insertions and deletions, while containing far fewer than the maximum possible number of substitutions.

SW or SW-Gotoh may be implemented using dynamic programming to perform local sequence alignment of the two strings, S and A, of sizes m and n, respectively. This dynamic programming employs tables or matrices to preserve match scores and avoid re-computation for successive cells. Each element of the string can be indexed with respect to a letter of the sequence, that is, if S is the string ATCGAA, S[1]=A.

Instead of representing the optimum alignment as Hi,j (above), the optimum alignment can be represented as B[j,k] in equation (2) below:

$$B[j,k] = \max(p[j,k], i[j,k], d[j,k], 0) (\text{for } 0 < j \le m, 0 < k \le n) \quad (2)$$

The arguments of the maximum function, B[j,k], are outlined in equations (3)-(5) below, wherein MISMATCH_PEN, MATCH_BONUS, INSERTION_PEN, DELETION_PEN, and OPENING_PEN are all constants, and all negative except for MATCH_BONUS (PEN is short for PENALTY). The match argument, p[j,k], is given by equation (3), below:

$$p[j, k] = \max(p[j-1, k-1], i[j-1, k-1], d[j-1, k-1]) + \quad (3)$$
$$\text{MISTMATCH\_PEN, if } S[j] \ne A[k] =$$
$$\max(p[j-1, k-1], i[j-1, k-1], d[j-1, k-1]) +$$
$$\text{MATCH\_BONUS, if } S[j] = A[k]$$

the insertion argument i[j,k], is given by equation (4), below:

$$i[j,k] = \max(p[j-1,k] + \text{OPENING\_PEN}, i[j-1,k], d[j-1,k] + \text{OPENING\_PEN}) + \text{INSERTION\_PEN} \quad (4)$$

and the deletion argument d[j,k], is given by equation (5), below:

$$d[j,k] = \max(p[j,k-1] + \text{OPENING\_PEN}, i[j,k-1] + \text{OPENING\_PEN}, d[j,k-1]) + \text{DELETION\_PEN} \quad (5)$$

For all three arguments, the [0,0] element is set to zero to assure that the backtrack goes to completion, i.e., p[0,0]=i[0,0]=d[0,0]=0.

The scoring parameters are somewhat arbitrary, and can be adjusted to achieve the behavior of the computations. One example of the scoring parameter settings (Huang, Chapter 3: Bio-Sequence Comparison and Alignment, ser. Curr Top Comp Mol Biol. Cambridge, Mass.: The MIT Press, 2002) for DNA would be:

MATCH_BONUS: 10
MISMATCH_PEN: −20
INSERTION_PEN: −40
OPENING_PEN: −10
DELETION_PEN: −5

The relationship between the gap penalties (INSERTION_PEN, OPENING_PEN) above help limit the number of gap openings, i.e., favor grouping gaps together, by setting the gap insertion penalty higher than the gap opening cost. Of course, alternative relationships between MISMATCH_PEN, MATCH_BONUS, INSERTION_PEN, OPENING_PEN and DELETION_PEN are possible.

In some embodiments, the methods and systems of the invention use a modified Smith-Waterman operation that involves a multi-dimensional look-back through the graph 231. Multi-dimensional operations of the invention provide for a "look-back" type analysis of sequence information (as in Smith-Waterman), wherein the look back is conducted through a multi-dimensional space that includes multiple pathways and multiple nodes. The multi-dimensional algorithm can be used to align sequence reads against the DAG-type reference. That alignment algorithm identifies the maximum value for Ci,j by identifying the maximum score with respect to each sequence contained at a position on the DAG (e.g., the reference sequence construct). In fact, by looking "backwards" at the preceding positions, it is possible to identify the optimum alignment across a plurality of possible paths.

The modified Smith-Waterman operation described here, aka the multi-dimensional alignment, provides exceptional speed when performed in a genomic DAG system that employs physical memory addressing (e.g., through the use of native pointers or index free adjacency as discussed above). The combination of multi-dimensional alignment to a graph 231 with the use of spatial memory addresses (e.g., native pointers or index-free adjacency) improves what the computer system is capable of, facilitating whole genomic scale analysis and epigenetic profiling to be performed using the methods described herein.

The operation includes aligning a sequence, or string, to a DAG. For the purpose of defining the algorithm, let S be the string being aligned, and let D be the directed acyclic graph to which S is being aligned. The elements of the string, S, are bracketed with indices beginning at 1. Thus, if S is the string ATCGAA. S[1]=A. S[4]=G, etc.

In certain embodiments, for the DAG, each letter of the sequence of a node will be represented as a separate element, d. A predecessor of d is defined as:

(i) If d is not the first letter of the sequence of its node, the letter preceding d in its node is its (only) predecessor;
(ii) If d is the first letter of the sequence of its node, the last letter of the sequence of any node (e.g., all exons upstream in the genome) that is a parent of d's node is a predecessor of d.

The set of all predecessors is, in turn, represented as P[d].

In order to find the "best" alignment, the algorithm seeks the value of M[j,d], the score of the optimal alignment of the first j elements of S with the portion of the DAG preceding (and including) d. This step is similar to finding Hi,j in equation 1 above. Specifically, determining M[j,d] involves finding the maximum of a, i, e, and 0, as defined below:

$$M[j,d]=\max\{a,i,e,0\} \quad (6)$$

where
e=max{M[j, p*]+DELETE_PEN} for p* in P[d]
i=M[j−1, d]+INSERT_PEN
a=max{M[j−1, p*]+MATCH_SCORE} for p* in P[d], if S[j]=d;
max{M[j−1, p*]+MISMATCH_PEN} for p* in P[d], if S[j]≠d As described above, e is the highest of the alignments of the first j characters of S with the portions of the DAG up to, but not including, d, plus an additional DELETE_PEN. Accordingly, if d is not the first letter of the sequence of the node, then there is only one predecessor, p, and the alignment score of the first j characters of S with the DAG (up-to-and-including p) is equivalent to M[j,p]+DELETE_PEN. In the instance where d is the first letter of the sequence of its node, there can be multiple possible predecessors, and because the DELETE_PEN is constant, maximizing [M[j, p*]+DELETE_PEN] is the same as choosing the predecessor with the highest alignment score with the first j characters of S.

In equation (6), i is the alignment of the first j−1 characters of the string S with the DAG up-to-and-including d, plus an INSERT_PEN, which is similar to the definition of the insertion argument in SW (see equation 1).

Additionally, a is the highest of the alignments of the first j characters of S with the portions of the DAG up to, but not including, d, plus either a MATCH_SCORE (if the jth character of S is the same as the character d) or a MISMATCH_PEN (if the jth character of S is not the same as the character d). As with e, this means that if d is not the first letter of the sequence of its node, then there is only one predecessor, i.e., p. That means a is the alignment score of the first j−1 characters of S with the DAG (up-to-and-including p), i.e., M[j−1,p], with either a MISMATCH_PEN or MATCH_SCORE added, depending upon whether d and the jth character of S match. In the instance where d is the first letter of the sequence of its node, there can be multiple possible predecessors. In this case, maximizing (M[j, p*]+MISMATCH_PEN or MATCH_SCORE) is the same as choosing the predecessor with the highest alignment score with the first j−1 characters of S (i.e., the highest of the candidate M[j−1,p*] arguments) and adding either a MISMATCH_PEN or a MATCH_SCORE depending on whether d and the jth character of S match.

Again, as in the SW algorithm, the penalties. e.g., DELETE_PEN, INSERT_PEN, MATCH_SCORE and MISMATCH_PEN, can be adjusted to encourage alignment with fewer gaps, etc.

As described in the equations above, the operation finds the optimal (e.g., maximum) value for the sequence 209 by calculating not only the insertion, deletion, and match scores for that element, but looking backward (against the direction of the DAG) to any prior nodes on the DAG to find a maximum score.

As shown in the lower portion of FIG. 6, any C appearing in the second sequence 615 can be taken to represent a methylated cytosine in the genome of the subject. Since the graph 231 may be gene- or genome-scale (e.g., millions of base-pairs long at its longest path), aligning the second sequence 615 to the graph 231 reveals where within the subject's genome the methylated cytosine lies. Thus, systems and methods of the invention may be used for calling 149 modified residues in the genome to produce epigenetic information 631 that identifies one or multiple modified bases and their locations within the genome of the subject.

Figure 7:
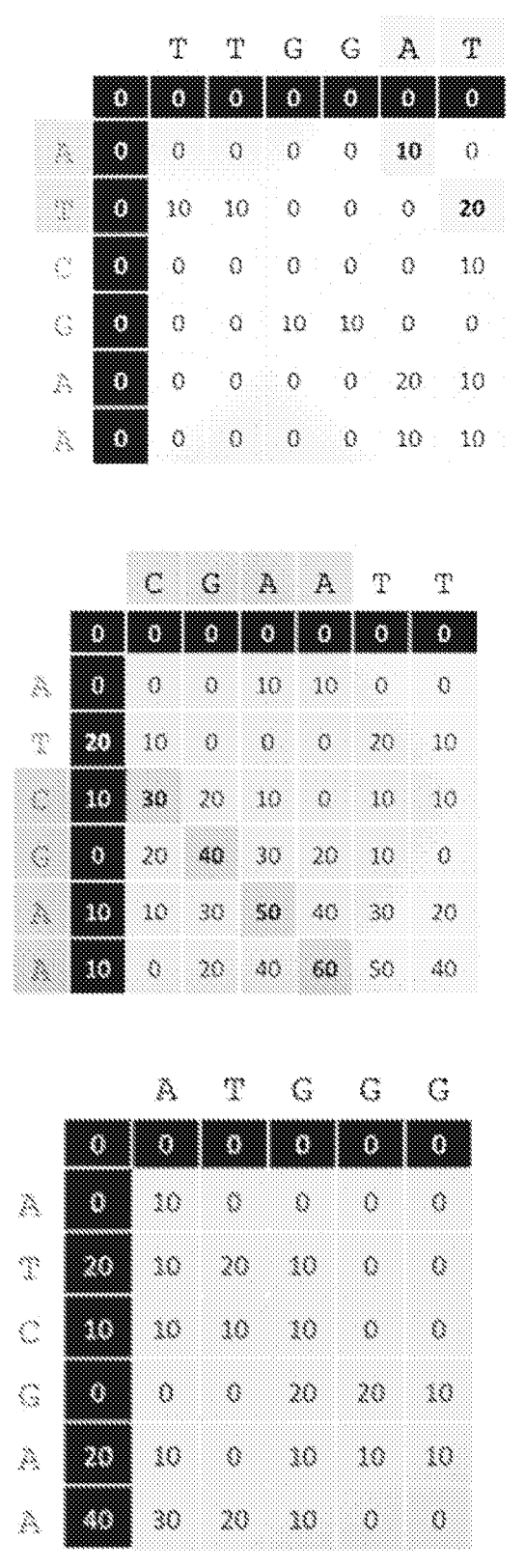

FIG. 7 shows the matrices that represent the comparison. The modified Smith-Waterman operation of the invention identifies the highest score and performs a backtrack to identify the proper alignment of the sequence. See. e.g., U.S. Pub. 2015/0057946 and U.S. Pub. 2015/0056613, both incorporated by reference. Systems and methods of the invention can be used to provide a report that identifies a modified base at the position within the genome of the subject.

Figure 8:
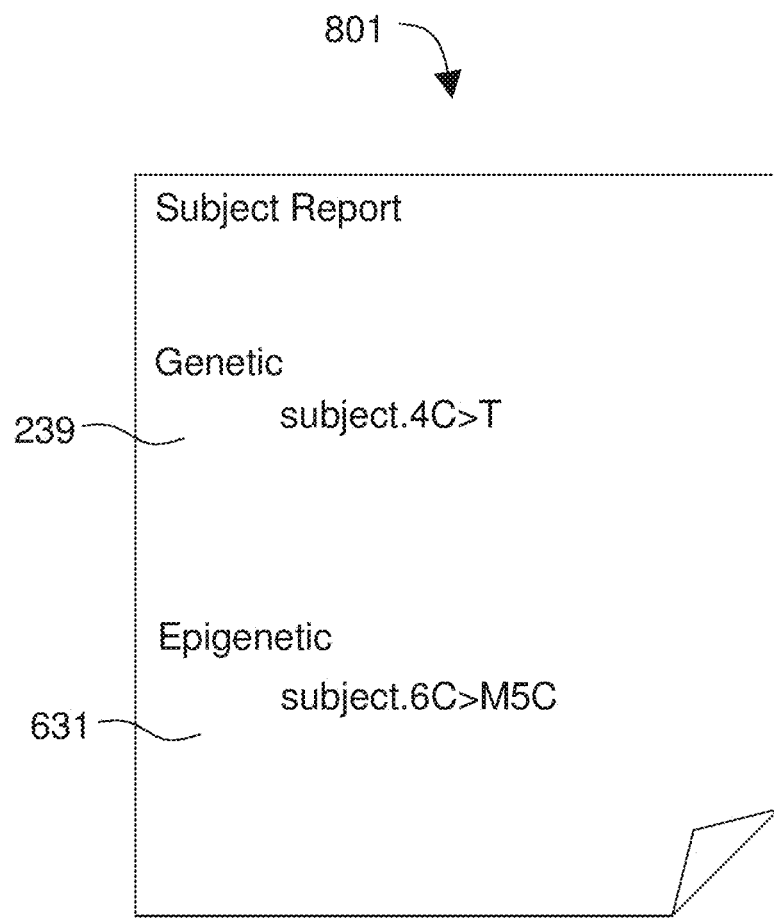
FIG. 8 illustrates a report profiling modified bases within the genome of the subject.

FIG. 8 illustrates a report 801 that identifies a modified base at the position within the genome of the subject. Report 801 includes epigenetic information 631 that identifies one or multiple modified bases and their locations within the genome of the subject. In certain embodiments, report 801 also includes genotype information 239 about un-modified bases in the subject's genome. Thus use of systems and methods of the invention provide a product that facilitates medical genetics and patient counseling. A physician may use a report 801 provided by the system to determine a medical course of action or counsel a patient on health and wellness issues.

Methods may be used to provide a report on phenomenon with clinical or developmental significance to a subject. For example, a report may identify a gene in the subject for which transcription has been regulated by the methylated cytosine at the position within the genome of the subject. In some embodiments, the report identifies a methylation status of a CpG island within the genome of the subject, for example, whether the CpG island is hyper- or hypo-methylated. Such a report may usefully determine whether CpG islands are hyper- or hypo-methylated, something that is often particularly biologically significant since CpG islands frequently occur in promoters of genes and hyper- or hypo-methylation of such sites can result in decreased or increased (respectively) expression of the associated genes.

It is understood that the addition of methyl groups to cytosine in certain CpG dinucleotides and patterns of methylated CpGs provide an epigenetic means for differential regulation of gene expression. It may be that CpG methylation regulates and stabilizes chromatin structure, influencing the ability of the transcription machinery to access regions of DNA. As a result, methylated CpGs may restrict transcription while unmethylated CpGs in the vicinity allow a gene to be expressed. Where a report 801 reveals a methylation status, such as a specific pattern, or hyper- or hypo-methylation, the report may provide insight into specific gene expression within a subject, and may be even be used to illustrate expression within specific tissue or cells. Discussion may be found in Saxonov et al., 2006, A genome-wide analysis of CpG dinucleotides in the human genome distinguishes two distinct classes of promoters, PNAS 103 (5):1412-1417, incorporated by reference.

It is noted that certain embodiments of systems and methods of the invention may be used for bisulfite conversion reaction that tend to be incomplete. In some treatments 129, incomplete bisulfite conversion may otherwise result in unmethylated Cs being called as methylated. Systems and methods of the invention may be used to address this problem by treating several different samples with bisulfite separately, and then sequencing and aligning as described above in connection with FIG. 6. Here, calling modified residues preferably includes calling a methylated cytosine at a position only when a C persists in each of the resulting aligned sequences. Additional discussion of methylation analysis may be found in Laird, 2010. Principles and challenges of genome-wide DNA methylation analysis, Nat Rev Genet 11:191-203; Zhang and Jeltsch, 2010, The application of next generation sequencing in DNA methylation analysis, Genes 1:85-101; and Lee et al., 2014. Improved reduced representation bisulfite sequencing for epigenomic profiling of clinical samples, Biological Procedures Online 16:1-9, the contents of each of which are incorporated by reference in their entirety for all purposes.

Figure 9:
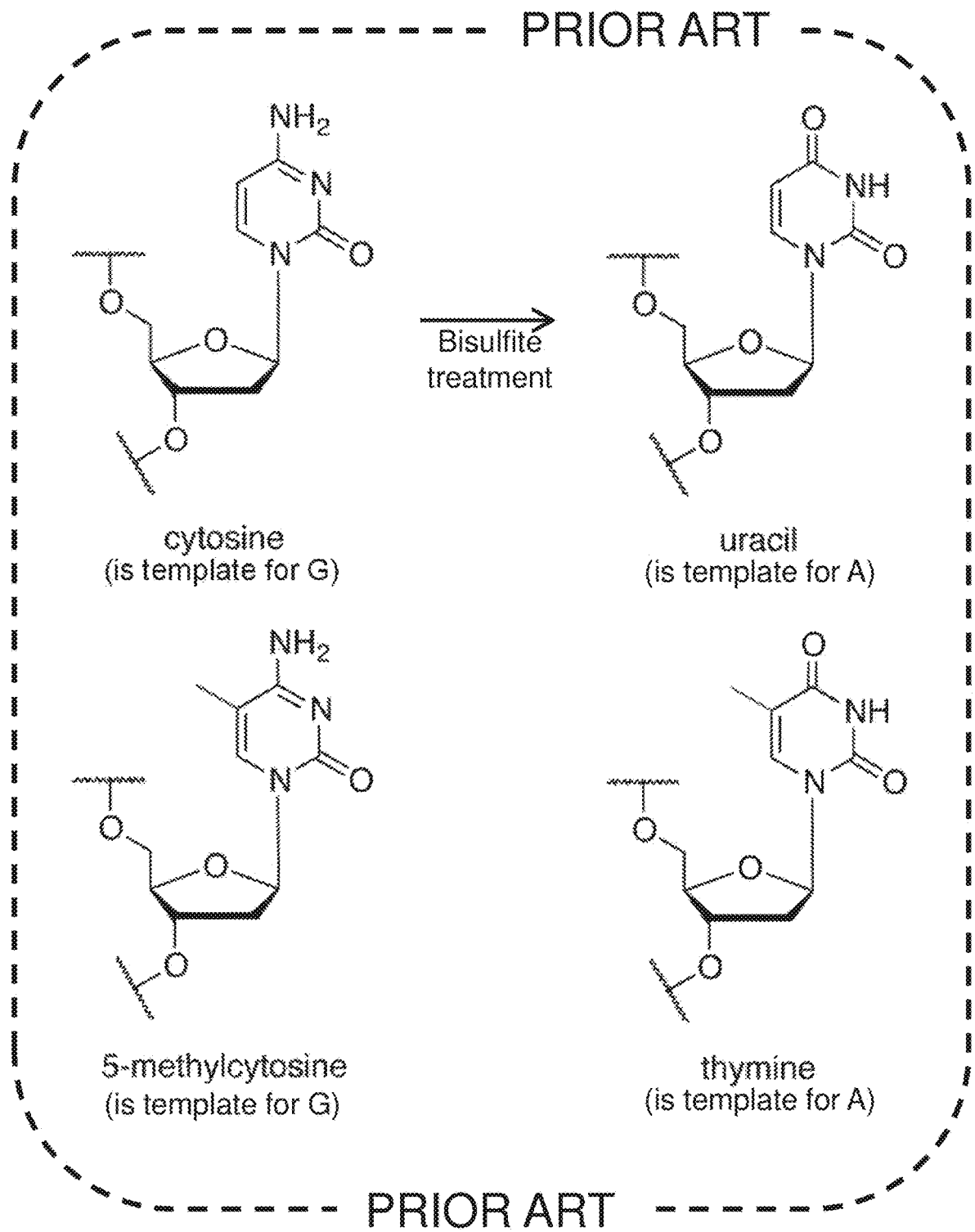
FIG. 9 gives a structure of certain pyrimidine nucleotides.

FIG. 9 gives a structure of common pyrimidine nucleotides that may be found in the subject genome to aid in visualizing the treatment and sequencing operations used in the invention. DNA methylation is a process by which a methyl group is added to a cytosine nucleotide. (Adenine nucleotides can also be methylated, but cytosine methylation is far more studied and better understood, so we will focus on cytosine methylation in this disclosure.) It typically occurs in CpG sites, ie when a C is followed in a genomic sequence by a G. Such groups are less prevalent than would be assumed given a random distribution of basepairs, something which may be attributed to the long-term effects of methylation. While deaminated cytosines are repaired, a methylated cytosine when deaminated is thymine, which is recognized as such during DNA replication. Thus after deamination, regions that had been methylated are not faithfully replicated and methylated CpGs in the germ line may be lost over time (Saxonov 2006). Methylation can affect the expression of a gene, typically repressing it, and is commonly implicated in cancer. In some contexts it may be heritable, and in this way it is also implicated in heritable diseases.

Methyl-Seq refers to the application of next-generation sequencing (NGS) methods to DNA that has been specially treated in order to make it possible to distinguish methylated from unmethylated cytosine. This involves treating the DNA with bisulfite, a process which converts unmethylated cytosine to uracil but leaves methylated cytosine unaffected. Remaining cytosine base-pairs can be assumed to be methylated. One complication is that the efficiency of the bisulfite conversion isn't absolute-some unmethylated cytosines will not be converted, and thus appear to be methylated.

Another complication that comes into play when using NGS methods is that PCR in the course of library preparation will turn the uracil nucleotides to thymine nucleotides, making it more difficult to recognize unmethylated cytosine and distinguish it from thymine (particularly thymine SNPs). (This happens because uracil binds with adenine in the first phase of PCR, and this adenine then bonds with thymine, which then bonds with adenine, etc.)

Additional material that may be useful in systems and methods of the invention may be found described in Lim et al., 2012, BatMeth: improved mapper for bisulfite sequencing reads on DNA methylation, Genome Biology 13:R82; Liu, 2012. Bis-SNP: Combined DNA methylation and SNP calling for bisulfite-seq data. Genome Biology 13:R61; Hoffman, 2005, Causes and consequences of DNA hypomethylation in human cancer. Biochem Cell Biol 83(3):296-321; and Zhang et al., 2011. Physical activity and global genomic DNA methylation in a cancer-free population, Epigenetics 6(3):293-299, the contents of each of which are incorporated by reference.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for determining epigenetic modifications in a first sequence of nucleotide bases representing at least a portion of a genome of a subject, the first sequence having been previously-obtained by sequencing nucleic acid from the subject, the method comprising:

using at least one processor to perform:

accessing a graph stored in at least one non-transitory memory, the graph representing, at each of a plurality of positions in the graph, a respective cytosine base of a plurality of cytosine bases in the first sequence and a respective thymine base of a plurality of thymine bases not in the first sequence, the graph comprising nodes and edges stored as objects in the at least one non-transitory memory, at least some of the objects including respective pointers to other objects representing other nodes, the nodes including:

a first node representing a cytosine base of the plurality of cytosine bases at a position of the plurality of positions, wherein the first node is stored as a first object in the at least one non-transitory memory, the first object comprising a first list of one or more pointers stored in the at least one non-transitory memory, and a second node representing a thymine base of the plurality of thymine bases at the position, wherein the second node is stored as a second object in the at least one non-transitory memory, the second object comprising a second list of one or more pointers stored in the at least one non-transitory memory; and aligning a second sequence of nucleotide bases to the graph to determine a proportion of a number of methylated cytosine bases to a total number of cytosine bases in at least the portion of the subject's genome, the second sequence representing at least the portion of the subject's genome and having been previously-obtained by sequencing bisulfite-treated nucleic acid from the subject, and the aligning comprising aligning the second sequence of nucleotide bases to the graph using (i) the objects including the first object and the second object, and (ii) the pointers including the first list of one or more pointers and the second list of one or more pointers.

2. The method of claim 1, further comprising determining the total number of cytosine bases in at least the portion of the subject's genome, the determining comprising:

determining a number of the plurality of cytosine bases in the first sequence.

3. The method of claim 2, wherein:

the second sequence comprises thymine bases, aligning the second sequence to the graph comprises aligning each of at least some of the thymine bases in the second sequence to a respective thymine base of the plurality of thymine bases not in the first sequence, and the method further comprises determining the number of methylated cytosine bases in at least the portion of the subject's genome at least in part by determining a number of the at least some of the thymine bases in the second sequence.

4. The method of claim 1, further comprising:

determining, based on the determined proportion of the number of methylated cytosine bases to the total number of cytosine bases in at least the portion of the subject's genome, whether transcription of a gene in the subject's genome has been regulated.

5. The method of claim 1, further comprising creating the graph in the at least one non-transitory memory using the first sequence, the creating comprising:

creating a first subset of the nodes of the graph, the first subset of the nodes including the first node and representing the first sequence; and creating a second subset of the nodes of the graph, the second subset of the nodes including the second node and representing the plurality of thymine bases not included in the first sequence.

6. The method of claim 1, further comprising:

identifying one or more variants in the first sequence of nucleotide bases.

7. The method of claim 1, wherein the portion of the subject's genome is at least 50% of a length of a chromosome of the subject's genome.

8. The method of claim 1, further comprising:

treating the nucleic acid from the subject with bisulfite to obtain the bisulfite-treated nucleic acid; and sequencing the bisulfite-treated nucleic acid.

9. A system, comprising:

at least one processor; and at least one non-transitory memory storing processor-executable instructions that, when executed by the at least one processor, cause the at least one processor to perform a method for determining epigenetic modifications in a first sequence of nucleotide bases representing at least a portion of a genome of a subject, the first sequence having been previously-obtained by sequencing nucleic acid from the subject, the method comprising:

accessing a graph stored in the at least one non-transitory memory, the graph representing, at each of a plurality of positions in the graph, a respective cytosine base of a plurality of cytosine bases in the first sequence and a respective thymine base of a plurality of thymine bases not in the first sequence, the graph comprising nodes and edges stored as objects in the at least one non-transitory memory, at least some of the objects including respective pointers to other objects representing other nodes, the nodes including:

a first node representing a cytosine base of the plurality of cytosine bases at a position of the plurality of positions, wherein the first node is stored as a first object in the at least one non-transitory memory, the first object comprising a first list of one or more pointers stored in the at least one non-transitory memory, and a second node representing a thymine base of the plurality of thymine bases at the position, wherein the second node is stored as a second object in the at least one non-transitory memory, the second object comprising a second list of one or more pointers stored in the at least one non-transitory memory; and aligning a second sequence of nucleotide bases to the graph to determine a proportion of a number of methylated cytosine bases to a total number of cytosine bases in at least the portion of the subject's genome, the second sequence representing at least the portion of the subject's genome and having been previously-obtained by sequencing bisulfite-treated nucleic acid from the subject, and the aligning comprising aligning the second sequence of nucleotide bases to the graph using (i) the objects including the first object and the second object, and (ii) the pointers including the first list of one or more pointers and the second list of one or more pointers.

10. The system of claim 9, further comprising:

determining, based on the determined proportion of the number of methylated cytosine bases to the total number of cytosine bases in at least the portion of the subject's genome, whether transcription of a gene in the subject's genome has been regulated.

11. The system of claim 9, further comprising creating the graph in the at least one non-transitory memory using the first sequence, the creating comprising:
creating a first subset of the nodes of the graph, the first subset of the nodes including the first node and representing the first sequence; and
creating a second subset of the nodes of the graph, the second subset of the nodes including the second node and representing the plurality of thymine bases not included in the first sequence.

12. The system of claim 9, wherein the portion of the subject's genome is at least 50% of a length of a chromosome of the subject's genome.

13. The system of claim 9, further comprising:
treating the nucleic acid from the subject with bisulfite to obtain the bisulfite-treated nucleic acid; and
sequencing the bisulfite-treated nucleic acid.

14. At least one non-transitory memory storing processor-executable instructions that, when executed by at least one processor, cause the at least one processor to perform a method for determining epigenetic modifications in a first sequence of nucleotide bases representing at least a portion of a genome of a subject, the first sequence having been previously-obtained by sequencing nucleic acid from the subject, the method comprising:
accessing a graph stored in the at least one non-transitory memory, the graph representing, at each of a plurality of positions in the graph, a respective cytosine base of a plurality of cytosine bases in the first sequence and a respective thymine base of a plurality of thymine bases not in the first sequence, the graph comprising nodes and edges stored as objects in the at least one non-transitory memory, at least some of the objects including respective pointers to other objects representing other nodes, the nodes including:
a first node representing a cytosine base of the plurality of cytosine bases at a position of the plurality of positions, wherein the first node is stored as a first object in the at least one non-transitory memory, the first object comprising a first list of one or more pointers stored in the at least one non-transitory memory, and
a second node representing a thymine base of the plurality of thymine bases at the position, wherein the second node is stored as a second object in the at least one non-transitory memory, the second object comprising a second list of one or more pointers stored in the at least one non-transitory memory; and
aligning a second sequence of nucleotide bases to the graph to determine a proportion of a number of methylated cytosine bases to a total number of cytosine bases in at least the portion of the subject's genome, the second sequence representing at least the portion of the subject's genome and having been previously-obtained by sequencing bisulfite-treated nucleic acid from the subject, and the aligning comprising aligning the second sequence of nucleotide bases to the graph using (i) the objects including the first object and the second object, and (ii) the pointers including the first list of one or more pointers and the second list of one or more pointers.

15. The at least one non-transitory memory of claim 14, further comprising:
determining, based on the determined proportion of the number of methylated cytosine bases to the total number of cytosine bases in at least the portion of the subject's genome, whether transcription of a gene in the subject's genome has been regulated.

16. The at least one non-transitory memory of claim 14, further comprising creating the graph in the at least one non-transitory memory using the first sequence, the creating comprising:
creating a first subset of the nodes of the graph, the first subset of the nodes including the first node and representing the first sequence; and
creating a second subset of the nodes of the graph, the second subset of the nodes including the second node and representing the plurality of thymine bases not included in the first sequence.

17. The at least one non-transitory memory of claim 14, further comprising:
treating at least a portion of the nucleic acid from the subject with bisulfite to obtain the bisulfite-treated nucleic acid; and
sequencing the bisulfite-treated nucleic acid.

18. A method for determining epigenetic modifications, the method comprising:
obtaining a nucleic acid previously obtained from a subject;
sequencing the nucleic acid to obtain a first sequence of nucleotide bases representing at least a portion of a genome of the subject;
creating a graph in at least one non-transitory memory using the first sequence, the graph representing, at each of a plurality of positions in the graph, a respective cytosine base of a plurality of cytosine bases in the first sequence and a respective thymine base of a plurality of thymine bases not in the first sequence, wherein creating the graph comprises storing objects in the at least one non-transitory memory, the objects representing nodes and edges connecting the nodes, at least some of the objects including respective pointers to other objects representing other nodes, the nodes including:
a first node representing a cytosine base of the plurality of cytosine bases at a position of the plurality of positions, wherein the first node is stored as a first object in the at least one non-transitory memory, the first object comprising a first list of one or more pointers stored in the at least one non-transitory memory, and
a second node representing a thymine base of the plurality of thymine bases at the position, wherein the second node is stored as a second object in the at least one non-transitory memory, the second object comprising a second list of one or more pointers stored in the at least one non-transitory memory;
treating the nucleic acid with bisulfite to obtain a bisulfite-treated nucleic acid;
sequencing the bisulfite-treated nucleic acid to obtain a second sequence of nucleotide bases; and
aligning the second sequence of nucleotide bases to the graph using (i) the objects including the first object and the second object, and (ii) the pointers including the first list of one or more pointers and the second list of one or more pointers.

19. The method of claim 18, further comprising:
identifying, based on a result of aligning the second sequence of nucleotide bases to the graph, a presence of at least one methylated cytosine in at least the portion of the subject's genome; and generating an output indicating the presence of the at least one methylated cytosine in at least the portion of the subject's genome.

20. The method of claim 18, further comprising:

determining, based on a result of aligning the second sequence of nucleotide bases to the graph, a proportion of a number of methylated cytosine bases to a total number of cytosine bases in at least the portion of the subject's genome.

* * * * *